(12) United States Patent
Masakari et al.

(10) Patent No.: US 11,066,690 B2
(45) Date of Patent: Jul. 20, 2021

(54) FLAVIN-BINDING GLUCOSE DEHYDROGENASE VARIANT

(71) Applicant: KIKKOMAN CORPORATION, Noda (JP)

(72) Inventors: Yousuke Masakari, Noda (JP); Chiaki Hara, Noda (JP)

(73) Assignee: KIKKOMAN CORPORATION, Noda (JP)

(*) Notice: Subject to any disclaimer, the term of this patent is extended or adjusted under 35 U.S.C. 154(b) by 0 days.

(21) Appl. No.: 16/099,779

(22) PCT Filed: May 9, 2017

(86) PCT No.: PCT/JP2017/017494
§ 371 (c)(1),
(2) Date: Nov. 8, 2018

(87) PCT Pub. No.: WO2017/195765
PCT Pub. Date: Nov. 16, 2017

(65) Prior Publication Data
US 2019/0136285 A1 May 9, 2019

(30) Foreign Application Priority Data
May 9, 2016 (JP) .............................. JP2016-093779

(51) Int. Cl.
| | |
|---|---|
| C12Q 1/00 | (2006.01) |
| C12Q 1/32 | (2006.01) |
| C12N 9/04 | (2006.01) |
| C12N 5/10 | (2006.01) |
| C12N 15/09 | (2006.01) |
| C12M 1/40 | (2006.01) |
| C12N 15/52 | (2006.01) |

(52) U.S. Cl.
CPC .............. *C12Q 1/006* (2013.01); *C12M 1/40* (2013.01); *C12N 5/10* (2013.01); *C12N 9/0006* (2013.01); *C12N 15/09* (2013.01); *C12N 15/52* (2013.01); *C12Q 1/32* (2013.01); *C12Y 101/05* (2013.01)

(58) Field of Classification Search
CPC ........ C12Q 1/006; C12Q 1/32; C12N 9/0006; C12N 5/10; C12N 15/09; C12N 15/52; C12Y 101/05
See application file for complete search history.

(56) References Cited

U.S. PATENT DOCUMENTS

2006/0063217 A1  3/2006  Omura et al.
2008/0014612 A1  1/2008  Tsuji et al.
2008/0220460 A1  9/2008  Kawaminami et al.
2009/0181408 A1  7/2009  Tanaka et al.
2010/0323378 A1  12/2010  Honda et al.
2011/0318810 A1  12/2011  Tajima et al.
2013/0168263 A1  7/2013  Sode et al.
2014/0287445 A1  9/2014  Tajima et al.
2014/0287478 A1  9/2014  Sumida et al.
2014/0302542 A1  10/2014  Araki et al.
2015/0031059 A1  1/2015  Sumida et al.
2016/0319246 A1  11/2016  Araki
2018/0340211 A1  11/2018  Masakari et al.
2018/0355022 A1  12/2018  Masakari et al.
2019/0185907 A1  6/2019  Masakari
2019/0257781 A1  8/2019  Masakari

FOREIGN PATENT DOCUMENTS

| EP | 2719761 A1 | 4/2014 |
|---|---|---|
| EP | 3112461 A1 | 1/2017 |
| JP | 2007-289148 A | 11/2007 |
| JP | 2008-237210 A | 10/2008 |
| JP | 4494978 B2 | 4/2010 |
| JP | 4648993 B2 | 12/2010 |

(Continued)

OTHER PUBLICATIONS

UniProt Accession No. A0A0C9MWY7, Alcohol oxidase. Created Apr. 29, 2015.*

(Continued)

*Primary Examiner* — Iqbal H Chowdhury
(74) *Attorney, Agent, or Firm* — Lucas & Mercanti, LLP

(57) ABSTRACT

The present invention relates to FAD-GDH consisting of the amino acid sequence of SEQ ID NO: 1 or 3, an amino acid sequence having an identity of 70% or more with the amino acid sequence of SEQ ID NO: 1 or 3, or an amino acid sequence having a deletion, substitution or addition of one or several amino acids in the amino acid sequence (the amino acid sequence of SEQ ID NO: 1 or the amino acid sequence having an identity of 70% or more with the amino acid sequence of SEQ ID NO: 1); having an amino acid substitution at the position(s) corresponding to the following amino acid(s): the amino acid at the 175th position in the amino acid sequence of SEQ ID NO: 1, the amino acid at the 214th position in the amino acid sequence of SEQ ID NO: 1, the amino acid at the 192nd position in the amino acid sequence of SEQ ID NO: 1, the amino acid at the 212th position in the amino acid sequence of SEQ ID NO: 1, the amino acid at the 218th position in the amino acid sequence of SEQ ID NO: 1, and/or the amino acid at the 226th position in the amino acid sequence of SEQ ID NO: 1; and having an improved thermal stability compared to that before the substitution, provided that an FAD-GDH consisting of the amino acid sequence of SEQ ID NO: 28, 30 or 32 is excluded.

6 Claims, 4 Drawing Sheets
Specification includes a Sequence Listing.

(56) References Cited

FOREIGN PATENT DOCUMENTS

| | | |
|---|---|---|
| JP | 2015-084676 A | 5/2015 |
| JP | 5873796 B2 | 3/2016 |
| JP | 2017-000137 A | 1/2017 |
| WO | 2007/139013 A1 | 12/2007 |
| WO | 2009/084616 A1 | 7/2009 |
| WO | 2012/169512 A1 | 12/2012 |
| WO | 2013/065623 A1 | 5/2013 |
| WO | 2013/065770 A1 | 5/2013 |
| WO | 2013/118798 A1 | 8/2013 |
| WO | 2013/118799 A1 | 8/2013 |
| WO | 2015/099112 A1 | 7/2015 |
| WO | 2015/129475 A1 | 9/2015 |

OTHER PUBLICATIONS

Sierks et al. Active Site Similarities of Glucose Dehydrogenase, Glucose Oxidase, and Glucoamylase Probed by Deoxygenated Substrates. Biochemistry, 1992, 31: 8972-8977.*

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Japanese Pharmaceutical and Food Safety Bureau of Ministry of Health, Labor and Welfare, "Pharmaceuticals and Medical Devices Safety Information No. 206", Oct. 2004, including partial English translation of relevant passages (17 pages).

Bak, Tchang-Gi; et al., BBA 65584, "Studies on the Glucose Dehydrogenase of Aspergillus Oryzae, I. Induction of Its Synthesis by p-Pensoquinone and Hydroquinone", Biochimica Et Biophysica Acta, vol. 139, Nov. 11, 1966, pp. 265-276.

Bak, Tchang-Gi, BBA 65585, "Studies on the Glucose Dehydrogenase of Aspergillus Oryzae, II. Purification and Physical and Chemical Properties", Biochimica Et Biophysica Acta, vol. 139, Nov. 11, 1966, pp. 277-293.

Bak, Tchang-Gi, BBA 65648, "Studies on the Glucose Dehydrogenase of Aspergillus Oryzae, III. General Enzymatic Properties", Biochimica Et Biophysica Acta, vol. 146, May 8, 1967, pp. 317-327.

Bak, Tchang-Gi; et al., BBA 65649, "Studies on the Glucose Dehydrogenase of Aspergillus Oryzae, IV. Histidyl Residue as an Active Site", Biochimica Et Biophysica Acta, vol. 146, May 16, 1967, pp. 328-335.

Database UniProt [Online], "Alcohol oxidase", Apr. 29, 2015, Database accession No. UniProt:A0A0C9MWY7, XP002794741 (2 pages).

Database UniProt [Online], "Uncharacterized protein", Apr. 1, 2015, Database accession No. UniProt:A0A0B7MYD9, XP002794742 (2 pages).

Database JPO Proteins [Online], "Novel Glucose Dehydrogenase", May 28, 2013, Database accession No. JPOP:DL578712, XP002794743 (1 page).

European Patent Office, "The Extended European Search Report", which was issued in connection with EP patent application No. 17796126.5, dated Oct. 16, 2019 (11 pages).

Sakai, Genki; et al., "Improvement of thermal stability of fungi-derived fad-dependent glucose dehydrogenase by introducing disulfide bond", Program Book, Engineering Conferences International (ECI), Enzyme Engineering XXII: Emerging Topics in Enzyme Engineering, Sep. 22-26, 2013, Toyama, Japan, Title page, pp. 105-112 and 190.

Sakai, Genki; et al., "Stabilization of fungi-derived recombinant FAD-dependent glucose dehydrogenase by introducing a disulfide bond", Biotechnol Lett, 2015, vol. 37(5), pp. 1091-1099.

Japanese Patent Office, "Notification of Third Party Submission", mailed Oct. 6, 2020, which was issued in connection with corresponding Japanese patent application No. 2018-517027, with list of references cited. (16 pages).

* cited by examiner

```
MpGDH  538 GDINSGEIEPGMNITSEDDLRSWLSNNVRSDWHPVGTCAMLPKELGGVVSPALMVYGTSN 597 (SEQ ID NO: 1)
MhGDH  535 ASINSGEIQPGSNITSDEDVKQWLADNVRSDWHPVGTCAMLPKELGGVVDSPDPNLLVYGTAN 594 (SEQ ID NO: 30)
MrdGDH 534 ASINSGEVEPGEKVQSDEDVRKWLSDNVRSDWHPVGTCAMLPKELGGVVDSPDPNLKVYGTAN 593 (SEQ ID NO: 32)
MsGDH  537 AALNSGEVEPGEKITDQDVRKWLADNVRSDWHPVGTCAMLPKRLGGVVDSPNLKVYGTAN 596 (SEQ ID NO: 94)
MgGDH  532 GDLNSGEVEPGMDITSDSDVRKWLADNVRSDWHPVGTCAMLPKELGGVVDSNLKVYGTAN 591 (SEQ ID NO: 28)
CsGDH  537 GDINSGETEPGKEITSDSDVRKWLADNVRSDWHPVGTCAMLPKELGGVVDPNLKVYGTSN 596 (SEQ ID NO: 95)
CrGDH  537 GDINSGETEPGKELTSDSDVRKWLADNVRSDWHPVGTCAMLPKELDGVVDPNLKVYGTSN 596 (SEQ ID NO: 96)
McGDH  539 GDLNSGEVEPGMNVTSEDDLRSWLSNNVRSDWHPVGTCAMLPQELGGVVSPALMVYGTSN 598 (SEQ ID NO: 97)

MpGDH  598 LRVVDASIMPLEVSSHLMQPTYGIAEKAADIIKNFYKTQHKNQN---- 641 (SEQ ID NO: 1)
MhGDH  595 LRVVDASIMPLEISSHLMQPTYGVAEKAADIIKMSRKNNN------- 635 (SEQ ID NO: 30)
MrdGDH 594 LRIVDASIIPLEISSHLMQPVYAVSERAADIIKSSSKK--------- 631 (SEQ ID NO: 32)
MsGDH  597 LRVVDASIIPLEISSHLMQPVYAVSERAADIIKG SRN--------- 633 (SEQ ID NO: 94)
MgGDH  592 LRVVDASIMPLEVSSHLMQPTFGVAEKAADIIKAEYKKQKAQ----- 633 (SEQ ID NO: 28)
CsGDH  597 LRVVDASIMPLEVSSHLMQPTEGIAEKAADIIKSANKKRSN------ 637 (SEQ ID NO: 95)
CrGDH  597 LRVVDASVMPLEVSSHLMQPTEGIAEKAADIIKSANKKRSN------ 637 (SEQ ID NO: 96)
McGDH  599 LRVVDASIMPLEVSSHLMQPTYGIAEKAADIIKNYYKSQYSGAGKN- 644 (SEQ ID NO: 97)
```

FLAVIN-BINDING GLUCOSE DEHYDROGENASE VARIANT

CROSS-REFERENCE TO RELATED APPLICATIONS

This application is a 371 of PCT/JP2017/017494, filed May 9, 2017, which claims benefit of Japanese Patent Application No. 2016-093779 filed on May 9, 2016.

TECHNICAL FIELD

The present invention relates to a flavin-binding glucose dehydrogenase having excellent thermal stability and/or reduced reactivity to maltose, a method for measuring glucose using the same, and a method for producing the flavin-binding glucose dehydrogenase.

BACKGROUND ART

Blood glucose concentration (blood glucose level) is an important marker for diabetes. As an apparatus for diabetic patients to manage their blood glucose levels, a wide variety of Self-Monitoring of Blood Glucose (SMBG) devices using an electrochemical biosensor are widely utilized. In the biosensors used in SMBG devices, an enzyme using glucose as a substrate such as glucose oxidase (GOD) has been employed up to the present. However, GOD employs oxygen as an electron acceptor and, therefore, in SMBG devices using GOD, oxygen dissolved in a measurement sample influences the measurement value, and an accurate measurement value may not be obtained.

On the other hand, glucose dehydrogenases (GDHs) are known as another type of enzyme using glucose as a substrate and not employing oxygen as an electron acceptor. For example, types of GDH using nicotinamide dinucleotide (NAD) or nicotinamide dinucleotide phosphate (NADP) as a coenzyme (NAD(P)-GDH), and a GDH using pyrroloquinoline quinone (PQQ) as a coenzyme (PQQ-GDH) have been found and are being used in biosensors of SMBG devices. However, NAD(P)-GDH has issues in that the stability of the enzyme is low and addition of a coenzyme is required: whereas, PQQ-GDH has issues in that the substrate specificity thereof is low and the same acts on sugar compounds (such as maltose. D-galactose and D-xylose) other than the measurement target, glucose, with the result that measurement values may be influenced by sugar compounds other than glucose present in measurement samples and accurate measurement values may not be obtained.

It has been recently reported that when the blood glucose level of a diabetic patient receiving infusion administration was measured by using an SMBG device employing a PQQ-GDH as the biosensor, the PQQ-GDH reacted with maltose contained in the infusion solution and a higher measurement value than the actual blood glucose level was obtained, and the patient developed hypoglycemia and the like due to treatment based on this value. It was also found that the same case will happen to patients who undergo a galactose load test as well as a xylose absorption test (see, for example, Non Patent Literature 1). In response to this, the Pharmaceutical and Food Safety Bureau of the Ministry of Health, Labour and Welfare conducted cross-reactivity tests in order to examine the effects of various types of saccharides, which are added to a glucose solution, on blood sugar measurement level. As a result, in the case where maltose (600 mg/dL), D-galactose (300 mg/dL) or D-xylose (200 mg/dL) was added, the measurement value by a blood glucose measurement kit using a PQQ-GDH was 2.5 to 3 times higher than the actual glucose concentration. In other words, it was found that the measurement values become inaccurate due to maltose, D-galactose or D-xylose which may be present in the measurement sample. Accordingly, there has been a strong need to develop GDH specifically measuring glucose with high substrate-specificity and without being influenced by sugar compounds which may be the cause of such measurement error.

Under the circumstances mentioned above, GDHs using a coenzyme other than the ones mentioned above are drawing attention. For example, although there is no specific description of substrate specificity, reports of GDHs from *Aspergillus oryzae* are known (see, for example, Non Patent Literatures 2 to 5). Furthermore, glucose dehydrogenases using flavin adenine dinucleotide (FAD) as a coenzyme (FAD-GDHs) from the genera *Aspergillus* and *Penicillium* are disclosed (see, for example, Patent Literatures 1 to 3). Moreover, an FAD-GDH from *Aspergillus* having reduced reactivity to D-xylose is disclosed (see, for example, Patent Literature 4).

While the above enzymes are less reactive to one or several types of sugar compounds that are not D-glucose; the enzymes do not have the characteristic that the reactivities thereof to each of maltose, D-galactose and D-xylose are sufficiently low. In contrast, an FAD-GDH found from the genus *Mucor*, which is a type of *mucor*, was shown to have excellent characteristics in that reactivity to each of maltose, D-galactose and D-xylose is sufficiently low (see, for example, Patent Literature 5). By using this GDH, glucose concentration can be accurately measured in the presence of maltose, D-galactose and D-xylose without being influenced by these sugar compounds (see, for example, Patent Literature 5). Such excellent substrate specificity is one characteristic of the FAD-GDH from *mucor* indicating the practical advantage thereof. Furthermore, Patent Literature 5 discloses the gene sequence and amino acid sequence of the FAD-GDH from *mucor*; as well as recombinant expression utilizing the gene sequence of the FAD-GDH from *mucor* in hosts such as *E. coli* and *Aspergillus oryzae*.

On the other hand, in order to improve convenience of self-blood glucose measurement, reduction in measurement time by further improving measurement sensitivity, reduction in size of a measurement system and reduction in the amount of required measurement sample and the like have been continuously pursued. For example, as a means to improve measurement sensitivity, it may be contemplated to increase the amount of glucose measuring enzyme to be loaded on the sensor. However, in the presence of a large amount of enzyme presumed in such use, even if said FAD-GDH from *Mucor* is used, reactions to maltose and D-xylose present in concentrations at or above a certain concentration are slightly observed and there is still room for improvement in reducing reactivities to sugar compounds other than D-glucose.

As an attempt to modify existing FAD-GDHs in order to improve the substrate specificity of FAD-GDH, a method of obtaining an FAD-GDH variant having reduced reactivity to D-xylose by introducing amino acid substitution into an FAD-GDH from *Aspergillus* is disclosed (see, for example, Patent Literatures 4 and 6). However, the FAD-GDH from *Aspergillus* has relatively quite high reactivity to D-xylose compared to the naturally occurring FAD-GDH from *Mucor*. Even if variants of the FAD-GDH from *Aspergillus* so far disclosed are used, it is difficult to state that they have sufficient substrate specificity. Patent Literature 7 discloses a method for obtaining an FAD-GDH variant having reduced reactivities to D-xylose and maltose by introducing amino acid substitution into the FAD-GDH from *Mucor*. However, attempts to confer further higher specificity are continuously needed.

Further, when considering use of an FAD-GDH in blood glucose sensors, the process of producing a sensor chip may comprise a step of heat-drying the enzyme and, therefore, an FAD-GDH with high heat resistance is needed. In particular, GOD is used in sensor chips used in continuous blood sugar measuring devices. One reason for this is that GODs are more superior in terms of thermal stability than FAD-GDHs and, therefore, suitable for long term measurements. In connection with such purpose, for example, an FAD-GDH from *mucor* having excellent substrate specificity and heat resistance (expressed in yeast of the genus *Zygosaccharomyces*), has been found, as disclosed in Patent Literature 4. Further, Patent Literature 8 discloses that heat resistance of an FAD-GDH from *mucor* is improved by introducing a site-specific mutation.

However, in consideration of the severe thermal conditions during production of sensor chips, attempts to confer further thermal stability are continuously needed.

CITATION LIST

Patent Literature

Patent Literature 1: JP Patent Publication (Kokai) No. 2007-289148
Patent Literature 2: JP Patent No. 4494978
Patent Literature 3: WO 07/139013
Patent Literature 4: JP Patent Publication (Kokai) No. 2008-237210
Patent Literature 5: JP Patent No. 4648993
Patent Literature 6: WO 09/084616
Patent Literature 7: WO 03/065770
Patent Literature 8: WO 12/169512

Non Patent Literature

Non Patent Literature 1: Pharmaceuticals and Medical Devices Safety Information No. 206, October, 2004, the Pharmaceutical and Food Safety Bureau of the Ministry of Health, Labor and Welfare
Non Patent Literature 2: Studies on the glucose dehydrogenase of *Aspergillus oryzae*. I. Induction of its synthesis by p-benzoquinone and hydroquinone, T. C. Bak, and R. Sato, Biochim. Biophys. Acta. 139, 265-276 (1967).
Non Patent Literature 3: Studies on the glucose dehydrogenase of *Aspergillus oryzae*. II. Purification and physical and chemical properties, T. C. Bak, Biochim. Biophys. Acta, 139, 277-293 (1967).
Non Patent Literature 4: Studies on the glucose dehydrogenase of *Aspergillus oryzae*. III. General enzymatic properties, T. C. Bak, Biochim. Biophys. Acta. 146, 317-327 (1967).
Non Patent Literature 5: Studies on the glucose dehydrogenase of *Aspergillus oryzae*. IV. Histidyl residue as an active site, T. C. Bak, and R Sato, Biochim. Biophys. Acta, 146, 328-335 (1967).

SUMMARY OF INVENTION

Technical Problem

An object of the present invention is to provide an FAD-GDH having excellent thermal stability and/or reduced reactivity to maltose.

Solution to Problem

As a result of conducting intensive studies in order to solve the above problems and searching for an FAD-GDH having improved thermal stability, the present inventors found that an FAD-GDH having improved thermal stability can be obtained by introducing a mutation into a known FAD-GDH. Further, as a result of searching for an FAD-GDH having reduced reactivity to maltose, the present inventors found that an FAD-GDH having reduced reactivity to maltose can be obtained by introducing a mutation into a known FAD-GDH.

More specifically, the present invention relates to the following items.

(1) An FAD-GDH consisting of the amino acid sequence of SEQ ID NO: 1 or 3, an amino acid sequence having an identity of 70% or more with the amino acid sequence of SEQ ID NO: 1 or 3, or an amino acid sequence having a deletion, substitution or addition of one or several amino acids in the amino acid sequence (the amino acid sequence of SEQ ID NO: 1 or the amino acid sequence having an identity of 70% or more with the amino acid sequence of SEQ ID NO: 1);

and having an amino acid substitution at the position(s) corresponding to the following amino acid(s);

the amino acid at the 175th position in the amino acid sequence of SEQ ID NO: 1, the amino acid at the 214th position in the amino acid sequence of SEQ ID NO: 1, the amino acid at the 192nd position in the amino acid sequence of SEQ ID NO: 1, the amino acid at the 212th position in the amino acid sequence of SEQ ID NO: 1, the amino acid at the 218th position in the amino acid sequence of SEQ ID NO: 1, and/or the amino acid at the 226th position in the amino acid sequence of SEQ ID NO: 1; and having an improved thermal stability compared to that before the substitution, provided that the FAD-GDH consisting of the amino acid sequence of SEQ ID NO: 28, 30 or 32 is excluded.

(2) An FAD-GDH consisting of the amino acid sequence of SEQ ID NO: 1 or 3, an amino acid sequence having an identity of 70% or more with the amino acid sequence of SEQ ID NO: 1 or 3, or an amino acid sequence having a deletion, substitution or addition of one or several amino acids in the amino acid sequence of SEQ ID NO: 1 or the amino acid sequence having an identity of 70% or more with the amino acid sequence of SEQ ID NO: 1, and having amino acid substitution at the position(s) corresponding to the following amino acid(s):

the amino acid at the position corresponding to the 175th position in the amino acid sequence of SEQ ID NO: 1 is cysteine, the amino acid at the position corresponding to the 214th position in the amino acid sequence of SEQ ID NO: 1 is cysteine, the amino acid at the position corresponding to the 192nd position in the amino acid sequence of SEQ ID NO: 1 is proline, the amino acid at the position corresponding to the 212th position in the amino acid sequence of SEQ ID NO: 1 is leucine or methionine, the amino acid at the position corresponding to the 218th position in the amino acid sequence of SEQ ID NO: 1 is histidine, and/or the amino acid at the position corresponding to the 226th position in the amino acid sequence of SEQ ID NO: 1 is any one of threonine, asparagine, alanine, serine, cysteine and valine;

provided that the FAD-GDH consisting of the amino acid sequence of SEQ ID NO: 28, 30 or 32 is excluded.

(3) An FAD-GDH consisting of the amino acid sequence of SEQ ID NO: 1 or 3, an amino acid sequence having an identity of 70% or more with the amino acid sequence of SEQ ID NO: 1 or 3, or an amino acid sequence having a deletion, substitution or addition of one or several amino acids in the amino acid sequence of SEQ ID NO: 1 or the amino acid sequence having an identity of 70% or more with the amino acid sequence of SEQ ID NO: 1; having amino acid substitution at the position corresponding to an amino acid at the 466th position in the amino acid sequence of SEQ ID NO: 1; and having a reduced reactivity to maltose compared to that prior to substitution.

(4) An FAD-GDH consisting of the amino acid sequence of SEQ ID NO: 1 or 3, an amino acid sequence having an identity of 70% or more with the amino acid sequence of SEQ ID NO: 1 or 3, or an amino acid sequence having a deletion, substitution or addition of one or several amino acids in the amino acid sequence of SEQ ID NO: 1 or the amino acid sequence having an identity of 70% or more with the amino acid sequence of SEQ ID NO: 1; wherein the position corresponding to the 466th position in the amino acid sequence of SEQ ID NO: 1 is substituted with aspartic acid, glutamic acid, arginine, lysine, histidine, asparagine, serine, glutamine, threonine, cysteine, alanine, tyrosine, phenylalanine, methionine, valine, leucine, tryptophan or isoleucine; and reactivity to maltose is reduced compared to that prior to substitution.

(5) An FAD-GDH wherein the amino acid at the position corresponding to the amino acid sequence of SEQ ID NO: 1 or 3 or an amino acid sequence having an identity of 70% or more with the amino acid sequence of SEQ ID NO: 1 or 3, or an amino acid sequence having a deletion, substation or addition of one or several amino acids in the amino acid sequence of SEQ ID NO: 1 or the amino acid sequence having an identity of 70% or more with the amino acid sequence of SEQ ID NO: 1 is an amino acid residue as follows:

the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is aspartic acid, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is glutamic acid, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is arginine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is lysine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is histidine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is asparagine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is serine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is glutamine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is threonine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is cysteine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is alanine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is tyrosine:

the amino acid at the position corresponding to alanine at the 175th position in the amino acid sequence of SEQ ID NO: 1 or 3 is cysteine, the amino acid at the position corresponding to asparagine at the 214th position is cysteine; and the amino acid at the position corresponding to glycine at the 466th position is phenylalanine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is methionine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is valine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is leucine, the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is tryptophan, or the amino acid at the position corresponding to alanine at the 175th position in the amino acid sequence of SEQ ID NO: 1 or 3 is cysteine; the amino acid at the position corresponding to asparagine at the 214th position is cysteine; and the amino acid at the position corresponding to glycine at the 466th position is isoleucine.

(6) An FAD-GDH gene encoding the FAD-GDH according to any of (1) to (5).

(7) A recombinant DNA comprising the FAD-GDH gene according to (6) inserted in a vector DNA.

(8) A host cell comprising the recombinant DNA according to (7) introduced thereinto.

(9) A method for producing an FAD-GDH, comprising the following steps of:
culturing the host cell according to (8),
expressing the FAD-GDH gene contained in the host cell, and
isolating the FAD-GDH from the culture.

(10) A method for measuring glucose using the FAD-GDH according to any of (1) to (5).

(11) A glucose assay kit comprising the FAD-GDH according to any of (1) to (5).

(12) A glucose sensor comprising the FAD-GDH according to any of (1) to (5).

Advantageous Effects of Invention

According to the present invention, it is possible to provide an FAD-GDH having excellent thermal stability and/or low reactivity to maltose.

BRIEF DESCRIPTION OF DRAWINGS

FIG. 1-1 shows a multiple alignment of GDHs derived from various species. MpGDH represents a GDH from *Mucor prainii* (SEQ ID NO: 1), MhGDH represents a GDH from *Mucor hiemalis* (SEQ ID NO: 30), MrdGDH represents a GDH from *Mucor* RD056860 (SEQ ID NO: 32), MsGDH represents a GDH from *Mucor subtilissimus* (SEQ ID NO: 94), MgGDH represents a GDH from *Mucor guilliermondii* (SEQ ID NO: 28), CsGDH represents a GDH from *Circinella simplex* (SEQ ID NO: 95), CrGDH represents a GDH from *Circinella* genus (SEQ ID NO: 96) and McGDH represents a GDH from *Mucor circinelloides* (SEQ ID NO: 97).

FIG. 1-2 shows the multiple alignment continued from FIG. 1-1.

FIG. 1-3 shows the multiple alignment continued from FIG. 1-2.

FIG. 1-4 shows the multiple alignment continued from FIG. 1-3.

DESCRIPTION OF EMBODIMENTS (Principle of Action of the FAD-GDH of the Present Invention and Method for Measuring the Activity Thereof)

The FAD-GDH of the present invention catalyzes the reaction of oxidizing a hydroxyl group of glucose in the presence of an electron acceptor to produce glucono-Δ-lactone.

The activity of the FAD-GDH of the present invention can be measured based on this principle of action and by using, for example, the following measurement system which employs phenazine methosulfate (PMS) and 2,6-dichloroindophenol (DCIP) as electron acceptors.

D-glucose+PMS (oxidized form)→D-glucono-Δ-lactone+PMS (reduced form)　　　(Reaction 1)

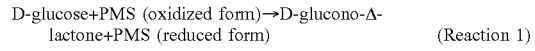

PMS (reduced form)+DCIP (oxidized form)→PMS (oxidized form)+DCIP (reduced form)　　　(Reaction 2)

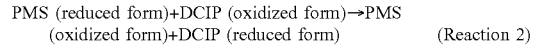

In (Reaction 1), as oxidation of glucose proceeds, PMS (reduced form) is generated. Subsequently, (Reaction 2) proceeds, in which as oxidation of PMS (reduced form) proceeds, DCIP is reduced. The degree of disappearance of "DCIP (oxidized form)" is detected as an amount of change in absorbance at a wavelength of 600 nm and the enzyme activity can be determined based on this amount of change in absorbance.

The activity of the FAD-GDH of the present invention is measured with the following procedure. First, 2.05 mL of 100 mM phosphate buffer (pH 7.0), 0.6 mL of 1M D-glucose solution and 0.15 mL of 2 mM DCIP solution are mixed and the mixture is kept at a temperature of 37° C. for 5 minutes. Then, to the mixture, 0.1 mL of a 15 mM PMS solution and 0.1 mL of the enzyme sample solution are added to initiate the reaction. Absorbance is measured at the initiation of the reaction and over time. The decrease (ΔA600) of absorbance at 600 nm per minute as the enzymatic reaction proceeds is obtained and GDH activity is calculated with the following formula. Herein, 1 U of GDH activity is defined as the amount of the enzyme required for reducing 1 μmol of DCIP at 37° C. in the presence of D-glucose (concentration 200 mM) per minute.

$$\text{GDH activity (U/mL)} = \frac{-(\Delta A600 - \Delta A600_{blank}) \times 3.0 \times df}{16.3 \times 0.1 \times 1.0} \quad \text{[Formula 1]}$$

Note that, in the formula, the numerical value 3.0 represents the amount (mL) of liquid (reaction reagent+enzyme reagent); the numerical value 16.3 represents the millimolar molecular extinction coefficient (cm²/μmol) under this activity measurement condition; the numerical value 0.1 represents the amount of the enzyme solution (mL); the numerical value 1.0 represents the optical path length of the cell (cm), ΔA600 blank represents the decrease in absorbance at 600 nm per minute in the case where the reaction is initiated by adding the buffer used for dilution of the enzyme in place of the enzyme sample solution; and the reference symbol, df represents the dilution factor.

(Amino Acid Sequence of the FAD-GDH of the Present Invention)

The FAD-GDH of the present invention consists of the amino acid sequence of SEQ ID NO: 1: an amino acid sequence having a high identity with said amino acid sequence, for example, an identity of preferably 70% or more, more preferably 75% or more, further preferably 80% or more, further preferably 85% or more, further preferably 90% or more, further preferably 95% or more, further preferably 97% or more, further preferably 98% or more, and most preferably 99% or more; or an amino acid sequence having a deletion, substitution or addition of one or several amino acids in the amino acid sequence, and has (comprises) a substitution of one or more amino acids at a position(s) corresponding to an amino acid(s) selected from the 175th, 214th, 192nd, 212th, 218th, 226th and 466th positions.

Preferably, the amino acid substitution at the position corresponding to said 175th position in the FAD-GDH of the present invention refers to the substitution of the amino acid at said position corresponding to the 175th position with cysteine: the amino acid substitution at said position corresponding to the 214th position refers to the substitution of the amino acid at said position corresponding to the 214th position with cysteine; the amino acid substitution at said position corresponding to the 192nd position refers to the substitution of the amino acid at said position corresponding to the 192nd position with proline; the amino acid substitution at said position corresponding to the 212th position refers to the substitution of the amino acid at said position corresponding to the 212th position with leucine or methionine; the amino acid substitution at said position corresponding to the 218th position refers to the substitution of the amino acid at said position corresponding to the 218th position with histidine; the amino acid substitution at said position corresponding to the 226th position refers to the substitution of the amino acid at said position corresponding to the 226th position with threonine, asparagine, serine, cysteine, alanine or valine; and the amino acid substitution at said position corresponding to the 466th position refers to the substitution of the amino acid at said position corresponding to the 466th position with aspartic acid, glutamic acid, arginine, lysine, histidine, asparagine, serine, glutamine, threonine, cysteine, alanine, tyrosine, phenylalanine, methionine, valine, leucine, tryptophan or isoleucine. Incidentally, in SEQ ID NO: 1, the amino acid not having the substitution of the present invention at the 175th position is alanine; at the 214th position is asparagine; at the 192nd position is serine; at the 212th position is isoleucine; at the 218th position is alanine; at the 226th position is isoleucine; and at the 466th position is glycine. In SEQ ID NO: 28, the position corresponding to the 175th position of SEQ ID NO: 1 not having the substitution of the present invention is threonine at the 170th position: the position corresponding to the 214th position of SEQ ID NO: 1 is asparagine at the 209th position; the position corresponding to the 218th position of SEQ ID NO: 1 is serine at the 213th position; the position corresponding to the 226th position of SEQ ID NO: 1 is isoleucine at the 221st position; and the position corresponding to the 466th position of SEQ ID NO: 1 is glycine at the 461st position. In SEQ ID NO: 30, the position corresponding to the 175th position of SEQ ID NO: 1 not having the substitution of the present invention is valine at the 172nd position: the position corresponding to the 214th position of SEQ ID NO: 1 is asparagine at the 211th position; and the position corresponding to the 466th position of SEQ ID NO: 1 is glycine at the 463rd position. In SEQ ID NO: 32, the position corresponding to the 175th position of SEQ ID NO: 1 not having the substitution of the present invention is valine at the 171st position: the position corresponding to the 214th position of SEQ ID NO: 1 is aspartic acid at the 210th position; and the position corresponding to the 466th position of SEQ ID NO: 1 is glycine at the 463rd position.

Among the FAD-GDHs of the present invention, examples of further preferable FAD-GDHs include multiple mutants, which comprise a plurality of the substitutions mentioned above in combination. For example, a double mutant having two of the substitutions mentioned above in combination and a triple mutant having three of the substitutions mentioned above in combination are encompassed by the present invention. By accumulating such mutations, an FAD-GDH having further improved thermal stability and further reduced reactivity to maltose can be produced.

When producing a multiple mutant as mentioned above, substitutions at positions other than those mentioned above can be used in combination. Even though such other substitutions at positions other than those at the predetermined positions above may not produce a remarkable effect when introduced in isolation unlike the substitutions at the predetermined positions above, if they are introduced in combination with the substitutions at the predetermined position(s), they may produce effects synergistically.

Further, in the FAD-GDH of the present invention, apart from the mutation(s) for improving thermal stability and the mutation(s) for reducing the reactivity to maltose, known mutations for providing other effects (advantages), such as mutations for improving temperature dependency and mutations for improving resistance to pH and predetermined substances and the like, may be introduced in combination. Such aspects in which other mutations are introduced in combination are encompassed by the present invention as long as they produce the effects (advantages) of the present invention.

As described below, the FAD-GDH of the present invention can also be obtained by first obtaining a gene encoding an amino acid sequence close to the amino acid sequence of SEQ ID NO: 1, by any method, and then introducing an amino acid substitution(s) at any of the positions equivalent to the predetermined positions in SEQ ID NO: 1.

Methods for introducing a desired amino acid substitution include a method of introducing a mutation at random and a method of introducing site-specific mutation at a predetermined position. Examples of the former method include an error-prone PCR method (Techniques, 1, 11-15. (1989)) and a method of using XL1-Red competent cells (manufactured by STRATAGENE) which readily produces errors in replication of a plasmid during proliferation and is prone to be modified. Examples of the latter method include a method of constructing a steric structure based on crystal structure analysis of a protein of interest, selecting an amino acid, which is predicted to provide a desired effect, based on the information, and introducing site-specific mutation by using, e.g., the commercially available Quick Change Site Directed Mutagenesis Kit (manufactured by STRATAGENE) and the like. Alternatively, as the latter method, there is a method of using the steric structure of a known protein having a high homology to a protein of interest, selecting an amino acid, which is expected to provide a desired effect, and introducing a site-specific mutation.

Further, for example, "the position corresponding to the amino acid sequence of SEQ ID NO: 1" as used herein refers to the same position in the alignment, when the amino acid sequence of SEQ ID NO: 1 is aligned with another FAD-GDH having an amino acid sequence identity with the sequence of SEQ ID NO: 1 (preferably 70% or more, more preferably 73% or more, more preferably 75% or more, more preferably 78% or more, further preferably 80% or more, further preferably 85% or more, further preferably 90% or more, further preferably 95% or more, further preferably 97% or more, further preferably 98% or more, most preferably 99% or more). Incidentally, amino acid sequence identity can be computed based on a program such as maximum matching and search homology of GENETYX Ver. 11 (manufactured by Genetics Inc.) or a program such as maximum matching and multiple alignment of DNASIS Pro (manufactured by Hitachi Software).

Further, as a method for specifying "the position corresponding to the amino acid sequence of SEQ ID NO: 1", for example, it is possible to compare amino acid sequences by using a known algorithm such as the Lipman-Pearson method and provide maximum identity with conserved amino acid residues present in the amino acid sequences of FAD-GDH. By aligning amino acid sequences of FAD-GDHs in this manner, if amino acid sequences of FAD-GDHs having an identity of 70% or more are compared, then, regardless of the presence of insertions and deletions in the amino acid sequences, it is possible to determine the positions of corresponding amino acid residues in the FAD-GDH sequences. Corresponding positions are presumably present at same positions of the three dimensional structure and have similar effects with respect to substrate specificity of the target FAD-GDHs.

(Homologous Region)

The amino acid sequence identity or similarity can be computed by using a program such as maximum matching or search homology of GENETYX Ver. 11 (manufactured by Genetics Inc.) or a program such as maximum matching or multiple alignment of DNASIS Pro (Hitachi Solutions Co., Ltd.). In order to compute amino acid sequence identity, positions having identical amino acids between two or more GDHs when the two or more GDHs are aligned can be investigated. Based on such information, identical regions between the amino acid sequences can be determined.

Further, positions having similar amino acids in two or more GDHs can be examined. For example, a plurality of amino acid sequences can be aligned using CLUSTALW. In this case, when a plurality of amino acid sequences are aligned by using Blosum62 as the algorithm and amino acids are determined as being similar, these amino acids may be referred to as similar amino acids. In the mutants of the present invention, an amino acid substitution(s) may be a substitution(s) that occurs between such similar amino acids. By such alignment, regions having identical amino acid sequences and positions occupied by similar amino acids in a plurality of amino acid sequences can be examined. Based on such information, a homologous region (conserved region) in an amino acid sequence can be determined.

In the present specification, the "homologous region" is specified as a region consisting of identical amino acids or similar amino acids at the corresponding positions between a standard GDH and a GDH to be compared when two or more GDHs are aligned and as a region consisting of continuous amino acids of 3 or more, 4 or more, 5 or more, 6 or more, 7 or more, 8 or more, 9 or more, or 10 or more. For example, in FIG. 1, GDHs having a full-length amino acid sequence identity of 70% or more were aligned. Of these, taking the GDH from the genus *Mucor* and of SEQ ID NO: 1 as the standard (basis), the region from the 31st to 41st position consists of identical amino acids, and, therefore, falls under (amounts to) a homologous region. Likewise, taking the GDH from the genus *Mucor* of SEQ ID NO: 1 the standard, the regions consisting of 58 to 62nd position. 71 to 85th position, 106 to 116th position, 119 to 127th position, 132 to 134th position, 136 to 144th position, 150 to 153rd position, 167 to 171st position. 219 to 225th position, 253 to 262nd position, 277 to 281st position, 301 to 303rd position, 305 to 312th position, 314 to 319th position, 324 to 326th position, 332 to 337th position, 339 to 346th position, 348 to 354th position, 386 to 394th position. 415 to 417th position, 454 to 459th position, 476 to 484th position. 486 to 491st position, 508 to 511st position, 518 to 520th position. 522 to 524th position, 526 to 528th position, 564 to 579th position, 584 to 586th position, 592 to 595th position, 597 to 599th position, 607 to 617th position and 625 to 630th position may fall under homologous regions.

The GDH of the present invention, when aligned with GDH having the amino acid sequence of SEQ ID NO: 1, has a full-length amino acid sequence identity of 50% or more, 55% or more, 60% or more. 65% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more. 98% or more, for example, 99% or more, and has glucose dehydrogenase activity. Further, the amino acid sequence in the homologous region of the GDH mutant of the present invention has a sequence identity of 80% or more, 81% or more, 82% or more, 83% or more, 84% or more, 85% or more, 86% or more, 87% or more. 88% or more, 89% or more, 90% or more, 91% or more, 92% or more, 93% or more, 94% or more, 95% or more. 96% or more, 97% or more, 98% or more, for example 99% or more, with the amino acid sequence of the homologous region in SEQ ID NO: 1.

Further, the position of a mutation of the present invention can be specified based on a homologous region. For example, the 175th position of SEQ ID NO: 1 or the position corresponding thereto can be specified as the position 4 amino acids away from the homologous region of the 167th to 171 st position toward the C terminal.

With regard to the FAD-GDH of the present invention, various variations within the range of the identity mentioned above are contemplated: however, as long as enzymological properties of FAD-GDHs are the same as those of the FAD-GDH of the present invention described in the present specification, they can be all included in the FAG-GDH of the present invention. The FAD-GDH having such an amino acid sequence is an FAD-GDH having high substrate specificity and sufficient thermal stability, and is industrially useful.

In the FAD-GDH of the present invention, while it is important that the amino acid at said position corresponding to the 175th position mentioned above is cysteine; the amino acid at said position corresponding to the 214th position is cysteine; the amino acid at said position corresponding to the 192nd position is proline; the amino acid at said position corresponding to the 212th position is leucine or methionine: the amino acid at said position corresponding to the 218th position is histidine; the amino acid at said position corresponding to the 226th position is threonine, asparagine, serine, alanine, cysteine or valine; or the amino acid at said position corresponding to the 466th position is aspartic acid, glutamic acid, arginine, lysine, histidine, asparagine, serine, glutamine, threonine, cysteine, alanine, tyrosine, phenylalanine, methionine, valine, leucine, tryptophan or isoleucine; it is not important whether the same is made by an artificial substitution procedure or not. For example, as in the case of the protein of SEQ ID NO: 1, when a protein, in which the original amino acid at the position above is different from the residue desired by the present invention, is used as the starting material and desired substitutions are introduced by known techniques, these desired amino residues are introduced by substitution. On the other hand, in the case where a desired protein is obtained totally by known peptide synthesis; in the case where a gene sequence is totally synthesized so as to encode the protein having a desired amino acid sequence, and a desired protein is obtained based on the same; or in the case where a protein originally having such a sequence is found in a naturally occurring protein, the FAD-GDH of the present invention can be obtained without carrying out any artificial substitution step.

(Improvement of Thermal Stability of the FAD-GDH of the Present Invention)

In the present invention, improvement of heat resistance is evaluated with conditions described in the method for measuring activity and method for measuring thermal stability described herein. Incidentally, pH during heat treatment in the present specification is 7.0. This is because the FAD-GDH of the present invention is developed in order to measure glucose (blood glucose level) in the blood and since the pH of blood is around neutral pH. By making evaluations under conditions as close to practical conditions as possible, more useful enzymes can be obtained.

The FAD-GDH of the present invention has the following residual activities under reaction conditions described in the method for measuring activity and method for measuring thermal stability described herein: a residual activity of 20% or more, preferably 30% or more, more preferably 35% or more, after a heat treatment, for example, at pH7.0 and 45° C. for 15 minutes: a residual activity of 1.3% or more, 2% or more, 5% or more. 10% or more, 15% or more, 20% or more, preferably 30% or more, more preferably 35% or more, after a heat treatment, for example, at pH7.0, 40° C. for 15 minutes; a residual activity of 1.3% or more, 2% or more, 5% or more, 10% or more, 15% or more, 20% or more, preferably 30% or more, more preferably 35% or more, after a heat treatment, for example, at pH7.0, 50° C. for 15 minutes; a residual activity of 1.3% or more, 2% or more, 5% or more, 10% or more, 15% or more, 20% or more, preferably 30% or more, more preferably 35% or more, after a heat treatment, for example, at pH7.0, 55° C. for 15 minutes; and a residual activity of 1.3% or more, 2% or more, 5% or more, 10% or more, 15% or more, 20% or more, preferably 30% or more, more preferably 35% or more, after a heat treatment, for example, at pH7.0, 60° C. for 15 minutes.

The modified FAD-GDH of the present invention is characterized in that the ratio of reactivity to maltose over reactivity to D-glucose (Mal/Glc (%)), when present in the same molar concentration and under the reaction conditions based on the method for measuring activity above, is decreased compared to the ratio prior to introduction of the amino acid substitution, preferably by 4% or more, 10% or more, 20% or more, more preferably 30% or more and further preferably 40% or more. That is, the ratio of reactivity to maltose over reactivity to D-glucose (Mal/Glc (%)) is preferably 2% or less, more preferably 1.5% or less, more preferably 1.0% or less, more preferably 0.8% or less, more preferably 0.7% or less and most preferably 0.6% or less.

Further, in addition to thermal stability being improved and substrate specificity to maltose being improved as described above, it is preferable for the FAD-GDH to also have other enzymatic properties more suitable for practical use. For example, it is preferable that the ratio of reactivity to D-xylose over reactivity to D-glucose (Xyl/Glc (%)) is 2% or less. For example, it is preferable that the specific activity is maintained at 60% or more, more preferably 65% or more, more preferably 70% or more, more preferably 75% or more, more preferably 80% or more, more preferably 85% or more and more preferably 90% or more, compared to that before a certain mutation is introduced. For example, it is preferable that the Km value is 110 mM or less and more preferably 100 mM or less.

(Obtaining a Gene Encoding the FAD-GDH of the Present Invention)

In order to efficiently obtain the FAD-GDH of the present invention, it is preferable to use genetic engineering techniques. In order to obtain a gene encoding the FAD-GDH of the present invention (hereinafter referred to as FAD-GDH gene), a gene cloning method commonly used may be employed. For example, in order to obtain the FAD-GDH of the present invention by modifying known FAD-GDH used as the starting material, chromosomal DNA or mRNA can be extracted from known microbial cells and various cells having FAD-GDH producing capability in accordance with routine methods, for example, methods described in Current Protocols in Molecular Biology (WILEY Interscience, 1989). Further, cDNA can be synthesized by using mRNA as the template. Using chromosomal DNA or cDNA thus obtained, a library of chromosomal DNA or cDNA can be prepared.

Next, an appropriate probe DNA can be synthesized based on the amino acid sequence information of a known FAD-GDH and an FAD-GDH gene having high substrate specificity can be screened from the library of chromosomal DNA or cDNA by using the probe DNA. Alternatively, an appropriate primer DNA can be prepared based on the amino acid sequence above and subjected to an appropriate polymerase chain reaction (PCR method) such as 5'RACE method and 3'RACE method to amplify DNA containing the gene fragment of interest encoding the FAD-GDH having high substrate specificity and then these DNA fragments can be linked to obtain DNA comprising a full-length FAD-GDH gene of interest.

As a method for starting from a known FAD-GDH and obtaining the FAD-GDH of the present invention having excellent thermal stability, a method can be adopted in which a mutation is introduced into the gene encoding the FAD-GDH which is the starting material and selection of the FAD-GDHs expressed by various mutant genes is carried out based on enzymological properties as the index (indicator).

Mutation for the starting FAD-GDH gene, can be performed by any known method depending on the intended form of mutation. That is, methods of bringing a chemical agent serving as a mutagen into contact with and allowing to act on the FAD-GDH gene or recombinant DNA having the gene integrated therein; ultraviolet irradiation methods; genetic engineering methods; or protein engineering methods, can be extensively used.

As the chemical agent serving as a mutagen in the above mutation treatment, hydroxylamine, N-methyl-N'-nitro-N-nitrosoguanidine, nitrous acid, sulfurous acid, hydrazine, formic acid or 5-bromouracil and the like can be mentioned.

Conditions for the contact and action can be determined depending on the type of chemical agent being used and the like and are not particularly limited as long as a desired mutation can actually be induced in the *Mucor*-derived FAD-GDH gene. A desired mutation can be induced usually by allowing the chemical agent to be in contact or act on the gene, preferably at a chemical agent concentration of 0.5 to 12 M and at a reaction temperature of 20 to 80° C. for 10 minutes or more, and preferably 10 to 180 minutes. In the case of ultraviolet irradiation, the irradiation can be performed in accordance with the routine method mentioned above (Chemistry today, p 24 to 30, 1989, June issue).

As a method employing a protein engineering procedure, in general, a method known as Site-Specific Mutagenesis can be used. Examples thereof include the Kramer method (Nucleic Acids Res., 12, 9441 (1984): Methods Enzymol., 154, 350 (1987): Gene, 37, 73 (1985)), the Eckstein method (Nucleic Acids Res., 13, 8749 (1985): Nucleic Acids Res., 13, 8765 (1985): Nucleic Acids Res. 14, 9679 (1986)) and the Kunkel method (Proc. Natl. Acid. Sci. U.S.A., 82, 488 (1985): Methods Enzymol., 154, 367 (1987)) and the like. Examples of a specific method for converting a nucleotide sequence in DNA include methods using commercially available kits (e.g., Transformer Mutagenesis Kit, Clontech; EXOIII:Mung Bean Deletion Kit, manufactured by Stratagene: Quick Change Site Directed Mutagenesis Kit, manufactured by Stratagene).

Alternatively, a method known as a general Polymerase Chain Reaction can be used (Technique, 1, 11 (1989)).

Incidentally, other than the above methods for modifying a gene, a modified FAD-GDH gene of interest having excellent thermal stability can be directly synthesized using organic synthesis methods or enzyme synthesis methods.

The nucleotide sequence of DNA of the FAD-GDH gene of the present invention selected by any method such as those mentioned above can be determined or confirmed by using, for example, multi-capillary DNA analysis system, CEQ2000 (manufactured by Beckman Coulter, Inc.).

(Examples of naturally occurring type FAD-GDHs from which the FAD-GDH of the present invention is derived) The FAD-GDH of the present invention can be obtained by modifying a known FAD-GDH. Suitable example of microorganisms from which known FAD-GDHs are derived include microorganisms classified in the subbranch *Mucor*, preferably the class *Mucor*, more preferably the order *Mucor* and further preferably the family *Mucor*. Specific examples thereof include FAD-GDHs derived from the genus *Mucor*, the genus *Absidia*, the genus *Actinomucor* and the genus *Circinella*.

Specific examples of preferable microorganism classified in the genus *Mucor* include *Mucor prainii, Mucor javanicus, Mucor circinelloides* f. *circinelloides, Mucor guilliermondii. Mucor hiemalis* f. *silvaticus, Mucor subtilissimus, Mucor dimorphosporus* and the like. More specific examples thereof include *Mucor prainii, Mucor javanicus, Mucor circinelloides* f. *circinelloides, Mucor guilliermondii* NBRC9403, *Mucor hiemalis* f. *silvalicus* NBRC6754. *Mucor subtilissimus* NBRC6338, *Mucor* RD056860, *Mucor dimorphosporus* NBRC5395 and the like described in Patent Literature 5. Specific examples of preferable microorganisms classified in the genus *Absidia* include *Absidia cylindrospora* and *Absidia hyalospora*. More specific examples thereof include *Absidia cylindrospora* and *Absidia hyalospora* described in Patent Literature 5. Specific examples of preferable microorganism classified in the genus *Actinomucor* include *Actinomucor elegans*. More specific examples thereof include *Actinomucor elegans* described in Patent Literature 5. Specific examples of preferable microorganism classified in the genus *Circinella* include *Circinella minor, Circinella mucoroides, Circinella muscae, Circinella rigida, Circinella simplex, Circinella umbellata. More specific examples thereof include Circinella minor* NBRC6448, *Circinella mucoroides* NBRC4453, *Circinella muscae* NBRC6410, *Circinella rigida* NBRC6411, *Circinella simplex* NBRC6412, *Circinella umbellata* NBRC4452, *Circinella umbellata* NBRC5842, *Circinella* RD055423 and *Circinella* RD055422. Incidentally, NBRC strains and RD strains are strains deposited in the NBRC (the Biotechnology Center of the National Institute of Technology and Evaluation).

(Vector Having an FAD-GDH of the Present Invention Gene Inserted Therein and Host Cell)

The FAD-GDH gene of the present invention obtained as described above can be integrated into a vector such as a bacteriophage, a cosmid or a plasmid for use in transformation of prokaryote cells or eukaryote cells in accordance with a routine method, and the host cells corresponding to the vectors can be transformed or transduced by a routine method.

Examples of the prokaryotic host cells include microorganisms belonging to the genus *Escherichia*, such as *E. coli* K-12 strain, *Escherichia coli* BL21 (DE3), *Escherichia coli* JM109, *Escherichia coli* DH5α, *Escherichia coli* W3110 and *Escherichia coli* C600 (all manufactured by Takara Bio Inc.). These microbial cells are transformed or transduced to obtain host cells (transformants) having DNA introduced thereinto. As a method for transferring a recombinant vector to such a host cell, in the case where the host cell is a microorganism belonging to *Escherichia coli*, a method of transferring (introducing) recombinant DNA in the presence of calcium ions can be employed. Furthermore, an electroporation method may be used. Moreover, commercially available competent cells (for example, ECOS Competent *Escherichia coli* BL21 (DE3): manufactured by Nippon Gene Co., Ltd.) may be used.

Examples of the eukaryotic host cell include yeast. Examples of microorganisms classified as yeast include yeasts belonging to the genus *Zygosaccharomyces*, the genus *Saccharomyces*, the genus *Pichia* and the genus *Candida*. The gene to be inserted may contain a marker gene which enables selection of transformed cells. Examples of the marker gene include genes which compensate auxotrophy of a host cell, such as URA3 and TRP1. The gene to be inserted may desirably contain a promoter enabling expression of the gene of the present invention in a host cell or other regulatory sequences (for example, enhancer sequence, terminator sequence, polyadenylation sequence). Specific examples of the promoter include GAL1 promoter and ADH1 promoter. As methods for transforming yeast, known methods such as the method of using lithium acetate (Methods Mol. Cell. Biol., 5, 255-269 (1995)) as well as electroporation (J Microbiol Methods 55 (2003) 481-484) can be suitably used. However, the transformation method is not limited to these and any method including the spheroplast method and glass bead method can be used for transformation.

Other examples of the eukaryotic host cell include cells of fungi such as the genus *Aspergillus* and the genus *Tricoderma*. The gene to be inserted desirably contain a promoter (for example, tef1 promoter), which enables expression of the gene of the present invention in host cells, and other regulatory sequences (for example, secretion signal sequence, enhancer sequence, terminator sequence, polyadenylation sequence and the like). The gene to be inserted may contain a marker gene, which enables selection of transformed cells, such as niaD and pyrG. Furthermore, the gene to be inserted may contain a homologous recombination region for insertion to an arbitrary chromosomal site. As a method for transforming a filamentous fungus cell, a known method, for example, a method of obtaining a protoplast, followed by using polyethylene glycol and calcium chloride (Mol. Gen. Genet., 218, 99-104 (1989)) can be suitably used.

(High-Throughput Screening)

A GDH can be further subjected to high throughput screening in order to obtain a functional GDH mutant. For example, a library of transformed strains or transduced strains comprising mutated GDH genes can be prepared and then the library may be subjected to high throughput screening based on a microtiter plate or to ultrahigh-throughput screening based on droplet microfluids. As an example, a combinatorial library of mutant genes encoding variants is constructed and then a large population of modified GDHs is screened by using phage display (for example, Chem. Rev. 105 (11): 4056-72, 2005); yeast display (for example, Comb Chem High Throughput Screen. 2008; 11 (2): 127-34); bacterial display (for example, Curr Opin Struct Biol 17: 474-80, 2007) and the like. Also see, Agresti et al, "Ultrahigh-throughput screening in drop-based microfluidics for directed evolution" Proceedings of the National Academy of Sciences 107 (9): 4004-4009 (March, 2010). The contents of this document on the ultrahigh-throughput screening method that may be used for screening GDH variants are incorporated herein by reference. A library can be constructed, for example, by an error-prone PCR method. Further, mutations may be introduced into the region(s) or position(s) described herein or the corresponding region(s) or position(s) thereto as the target by using saturation mutagenesis to construct a library. Using such library, appropriate cells such as electrocompetent EBY-100 cells, can be transformed and about 10 to the power of seven mutants can be obtained. Yeast cells transformed with the library can be subsequently subjected to cell sorting. A polydimethoxylsiloxane (PDMS) microfluidic device prepared by a standard soft lithography method may be used. Monodispersed droplets can be formed using a flow focus device. Formed droplets containing individual mutants can be subjected to an appropriate sorting device. When screening cells, the presence or absence of GDH activity can be utilized. For this purpose, a reaction solution having a composition that can develop color if GDH functions (acts thereon), may be used for example. For example, in the case of using DCIP, absorbance at 600 nm may be measured using a 96 well plate, a 192 well plate, a 384 well plate or a 9600 well plate and a plate reader. Mutation and screening can be repeated a plurality of times.

(Production of the FAD-GDH of the Present Invention)

The FAD-GDH of the present invention may be produced by culturing a host cell capable of producing the FAD-GDH of the present invention and obtained as mentioned above, expressing the FAD-GDH gene contained in the host cell, and then, isolating the FAD-GDH from the culture.

As the culture medium for culturing the host cell above, a culture medium prepared by adding one or more nitrogen sources such as yeast extract, tryptone, peptone, meat extract, corn steep liquor or soy or wheat bran steep liquor and one or more inorganic salts such as sodium chloride, primary potassium phosphate, secondary phosphate, magnesium sulfate, magnesium chloride, ferric chloride, ferric sulfate or manganese sulfate, and if necessary, further adding a sugar source and vitamins and the like, is used.

The initial pH of a culture medium is not limited; however the pH can be adjusted to 6 to 9 for example.

Culturing may be performed at a culture temperature of 10 to 42° C., preferably about 25° C., for 4 to 24 hours, and further preferably performed at a culture temperature of about 25° C. for 4 to 8 hours, in accordance with, e.g., aeration stirring deep culture, shaking culture or static culture.

After completion of culture, the FAD-GDH of the present invention is recovered from the culture. This can be carried out by a known enzyme sampling means routinely used.

For example, the fungus body can be subjected to a routine treatment such as a ultrasonication disruption treatment or a grinding treatment; or the FAD-GDH of the invention can be extracted by using a lytic enzyme such as lysozyme. Alternatively, the fungus body can be shaken or allowed to stand in the presence of toluene or the like to cause cell lysis, and the FAD-GDH of the invention can be discharged out of the fungus body. Subsequently, the lysis solution is filtered or centrifuged and solid matter is removed and if necessary, nucleic acids are removed by streptomycin sulfate, protamine sulfate or manganese sulfate and the like. Then, to the resultant solution, ammonium sulfate, an alcohol or acetone and the like is added, the mixture is fractionated and the precipitate is collected to obtain a crude enzyme of the FAD-GDH of the present invention.

The crude enzyme of the FAD-GDH of the present invention can be further purified by any known means. A purified enzyme preparation can be obtained by a method appropriately selected from, for example, a gel filtration method using Sephadex, ultrogel or bio gel; an adsorption elution method using an ion exchanger; an electrophoretic method using, e.g., polyacrylamide gel; an adsorption elution method using hydroxyapatite: a sedimentation method such as a sucrose density gradient centrifugation method; an affinity chromatography method; and a fractionation method using, e.g., a molecular sieve membrane or a hollow fiber membrane, or by using these methods in combination. In this manner, a purified FAD-GDH enzyme preparation of the present invention can be obtained.

(Method for Measuring Glucose with the FAD-GDH of the Present Invention)

The present invention discloses a glucose assay kit comprising the FAD-GDH of the present invention. Glucose in the blood (blood glucose level) can be measured by using the FAD-GDH of the present invention.

The glucose assay kit of the present invention comprises a modified FAD-GDH of the present invention in an amount sufficient for at least one assay. Typically, the glucose assay kit of the present invention comprises, other than the modified FAD-GDH of the present invention, a buffer solution required for the assay, a mediator and a glucose standard solution for preparing a calibration curve. The modified FAD-GDH to be used in the glucose measuring method and the glucose assay kit of the present invention can be provided in various forms, for example, as a freeze dried reagent or a solution prepared by dissolving the FAD-GDH in a proper preservation solution.

Measurement of glucose concentration in the case of a colorimetric glucose assay kit is, for example, carried out as follows. In the reaction layer of the glucose assay kit, a liquid or solid state composition containing FAD-GDH, an electron receptor and at least one selected from the group consisting of N-(2-acetamide)imide diacetate (ADA), bis(2-hydroxyethyl)iminotris(hydroxymethyl) methane (Bis-Tris), sodium carbonate and imidazole, as a reaction accelerator, are retained. A pH buffer and a coloring reagent can be added according to need. To this, a sample containing glucose is added and allowed to react for a predetermined time. During this time period, the absorbance of an electron acceptor discolored by reduction or a dye generated by polymerization upon receiving an electron from an electron receptor, at a wavelength corresponding to the maximum absorption wavelength, is monitored. The glucose concentration in a sample can be computed from the rate of change of absorbance per time if a rate method is employed; or computed from a change of absorbance up to the time point where glucose in the sample is completely oxidized if an endpoint method is employed, based on a calibration curve prepared in advance using a standard-concentration glucose solution.

Examples of the mediator and the coloring reagent to be used in this method include 2,6-dichlorophenolindophenol (DCPIP), which can be added as an electron acceptor and the amount of glucose can be determined by monitoring a decrease in absorbance at 600 nm. Glucose concentration can be computed by adding phenazine methosulfate (PMS) as an electron acceptor and nitrotetrazolium blue (NTB) as a coloring reagent and measuring the absorbance at 570 nm to determine the amount of diformazan generated. Incidentally and needless to mention, the electron acceptor and coloring reagent to be used herein are not limited to the above.

(Glucose Sensor Comprising the FAD-GDH of the Present Invention)

The present invention further discloses a glucose sensor comprising the FAD-GDH of the present invention. As an electrode, a carbon electrode, a gold electrode or a platinum electrode and the like is used and the FAD-GDH of the present invention is immobilized onto the electrode. Examples of the immobilization method include a method using a cross-linking agent, a method of embedding the FAD-GDH in a polymer matrix, a method of coating (covering) with a dialysis membrane and a method of using a photo-crosslinkable polymer, conductive polymer or redox polymer and the like. Alternatively, the FAD-GDH may be immobilized in a polymer or may be immobilized by adsorption on an electrode, together with an electron mediator such as ferrocene or a derivative thereof. Further, these methods may be used in combination. Typically, the FAD-GDH of the present invention is immobilized onto a carbon electrode by using glutaraldehyde and treated thereafter with a reagent having an amine group to block glutaraldehyde.

Glucose concentration can be measured as follows. To a constant-temperature cell, a buffer solution is added and the temperature is held constant. As the mediator, potassium ferricyanide or phenazine methosulfate and the like can be used. An electrode to which a modified FAD-GDH of the present invention is immobilized is used as the working electrode, and a counter electrode (for example, platinum electrode) and a reference electrode (for example, Ag/AgCl electrode) are used. A constant voltage is applied to the carbon electrode and after the current becomes stationary, a sample containing glucose is added and an increase of current is measured. Based on a calibration curve prepared by using a standard-concentration glucose solution, the glucose concentration of the sample can be calculated.

As a specific example, 1.5 U of the FAD-GDH of the present invention is immobilized to a glassy carbon (GC) electrode and the response current value corresponding to the glucose concentration is measured. To an electrolytic cell, 1.8 ml of 50 mM potassium phosphate buffer (pH 6.0) and 0.2 ml of aqueous 1 M hexacyano iron (III) potassium (potassium ferricyanide) solution are added. A GC electrode is connected to a potentiostat BAS 100B/W (manufactured by BAS) and the solution is stirred at 37° C., and then, a voltage of +500 mV is applied to a silver/silver chloride (saturated KCl) reference electrode. To this system, a 1 M D-glucose solution is added so as to obtain a final concentration of 1, 2, 3, 4, 5, 10, 20, 30, 40 and 50 mM and the current value at a constant state is measured for each addition. These current values are plotted relative to the corresponding glucose concentrations already known (1, 2, 3, 4, 5, 10, 20, 30, 40 and 50 mM) to obtain a calibration curve. In this manner, the amount of glucose can be determined by using an enzyme-immobilized electrode comprising the FAD binding glucose dehydrogenase of the present invention.

The present invention will be more specifically described by way of the following Examples. However, the technical scope of the present invention is not limited by these examples in any way.

EXAMPLES

In the present invention, the thermal stability and substrate specificity of modified FAD-GDHs were evaluated in accordance with the method described in the following Experimental Example unless otherwise specified.

Experimental Example (1) Preparation of Yeast Transformants Expressing Modified FAD-GDHs In accordance with a method described in Patent Literature 8, a recombinant plasmid (pYES2C-Mp (wild type)) encoding the FAD-GDH gene (wild type MpGDH gene) from *Mucor prainii* of SEQ ID NO: 2, was obtained.

Using the resultant recombinant plasmid pYES2C-Mp as the template and synthetic nucleotides for introducing substitutions of amino acids and KOD-Plus-(manufactured by Toyobo Co., Ltd.), PCR was performed in the following conditions.

More specifically, 5 µl of a 10×KOD-Plus-buffer solution, 5 µl of a mixed solution of dNTPs prepared so as to contain each of dNTPs at a concentration of 2 mM, 2 µl of a 25 mM $MgSO_4$ solution, 50 ng of pYES2C-Mp serving as the template, the above synthetic oligonucleotides (15 µmol for each) and 1 unit of KOD-Plus—were added and then sterile water was added up to a total amount of 50 µl to prepare the "reaction solution". The reaction solution thus prepared was subjected to a thermal cycler (manufactured by Eppendorf) in which incubation was performed at 94° C. for 2 minutes, and then, a cycle of a reaction at "94° C., 15 seconds", a reaction at "55° C., 30 seconds" and a reaction at "68° C., 8 minutes" was repeated 30 times.

After the treatment above, an aliquot was taken from the reaction solution and subjected to electrophoresis on a 1.0% agarose gel and it was confirmed that DNA of about 8 kbp was specifically amplified. The amplified DNA was treated with the restriction enzyme DpnI (manufactured by New England Biolabs), and then transformation was carried out by adding the same to competent cells of *E. coli* JM109 strain (manufactured by Nippon Gene Co., Ltd.) in accordance with the attached protocol. Then, each of the transformants obtained was inoculated to the LB-amp agar medium and cultured. The grown colonies were inoculated in the LB-amp liquid medium and subjected to shake culture and plasmid DNAs (for example, pYES2C-Mp-A175C/N214C in Example 1 and the like) containing the amplified DNA of about 8 kbp were isolated using the GenElute Plasmid Miniprep Kit (manufactured by Sigma) in accordance with the protocol attached to the kit. Then, the nucleotide sequences of the DNAs encoding the MpGDH gene in these plasmid DNAs were determined by using a multicapillary DNA analysis system, CEQ2000 (manufactured by Beckman Coulter, Inc.) and it was confirmed that in each of the sequences, the amino acids at the predetermined positions in the amino acid sequence of SEQ ID NO:

1 were substituted. In this manner, a yeast expression vector, pYES2C-Mp encoding a modified MpGDH having predetermined amino acid substitutions (modified form, for example, pYES2C-Mp-A175C/N214C) was obtained.

Thereafter, INVSc1 strain (manufactured by Invitrogen) was transformed with pYES2C-Mp (wild type) and pYES2C-Mp having mutations introduced thereinto (modified form, for example, pYES2C-Mp-A175C/N214C) by using a transformation kit for *S. cerevisiae* (manufactured by Invitrogen). In this manner, a yeast transformant, Sc-Mp (wild type) strain expressing wild type MpGDH, and yeast transformants, Sc-Mp strains expressing modified-type MpGDHs (modified form, for example, Sc-Mp-A175C/N214C) were obtained.

(2) Evaluation of Thermal Stability of FAD-GDH Expressed by Yeast

A yeast transformant Sc-Mp (wild type) and yeast transformants Sc-Mp (modified form, for example, Sc-Mp-A175C/N214C) each were cultured in 5 mL of a liquid pre-culture medium [0.67% (w/v) amino acid-free yeast nitrogen base (BD). 0.192% (w/v) additive for uracil-free yeast synthesis dropout medium (manufactured by Sigma), 2.0% (w/v) raffinose] at 30° C. for 24 hours. Thereafter. 1 mL of the liquid pre-culture medium was added in 4 mL of a main liquid culture medium [0.67% (w/v) amino acid-free yeast nitrogen base, 0.192% (w/v) additive for uracil-free yeast synthesis dropout medium, 2.5% (w/v) D-galactose, 0.75% (w/v) raffinose] and cultured at 30° C. for 16 hours. The culture liquid was centrifuged (10,000×g, 4° C., 3 minutes) to separate fungus bodies and the culture supernatant. The culture supernatant was used in evaluation of thermal stability.

The thermal stability of FAD-GDH was evaluated as follows. First, the culture supernatant containing a target FAD-GDH to be evaluated and recovered as described above was diluted with a dilution solution for an enzyme (100 mM potassium phosphate buffer (pH7.0)) so as to obtain a concentration of about 1 U/mL. Then, two samples (0.1 mL) were prepared from the enzyme solution. One of them was stored at 4° C., and the other was subjected to heat treatment at 45° C. for 15 minutes. After the heat treatment, the FAD-GDH activities of individual samples were measured. Taking (regarding) the enzyme activity of the sample stored at 4° C. as 100, the activity value of the sample treated at 45° C. for 15 minutes was determined as an "activity residual ratio (%)". The activity residual ratio (%) was used as an index for evaluating heat resistance of the various FAD-GDHs.

As a result of using the culture supernatant of Sc-Mp (wild type) strain expressing a wild type MpGDH, and evaluating the thermal stability of the wild type MpGDH, the residual activity ratio of the wild type MpGDH after the heat treatment of 45° C. for 15 minutes was 0%. As such, if the residual activity ratio of a modified MpGDH after the heat treatment is higher than 0%, it can be determined that the thermal stability of MpGDH is improved.

(3) Evaluation of Substrate Specificity

Substrate specificity was also evaluated by using yeast culture supernatants recovered in accordance with the manner as in the above (2), similar to the evaluation of thermal stability. First, the substrate of the method for measuring activity above was changed from D-glucose to a system containing maltose at the same molar concentration and the activities of each supernatant to the substrate were measured. Based on these values, "the ratio of reactivity to maltose over reactivity to D-glucose (Mal/Glc (%))" was calculated. When taking the Mal/Glc (%) value of the FAD-GDH from *Mucor* before introduction of site-specific mutation as 100%, the "Mal/Glc ratio" of the modified FAD-GDH after a site-specific mutation was introduced representing a relative substrate specificity was calculated for each of the mutants. In a modified FAD-GDH with a "Mal/Glc ratio" below 100, the reactivity to maltose decreases, compared to FAD-GDH before site-specific mutation was introduced meaning that substrate specificity is increased and the degree thereof is increased as the numerical value decreases.

The (Mal/Glc (%)) of the wild type MpGDH expressed by Sc-Mp (wild type) strain was 0.8%. While such substrate specificity is very excellent when compared to those of other FAD-GDHs conventionally known, under conditions where a large amount of enzyme is present, reactivity to maltose present in a predetermined concentration or more is slightly observed and there is still room for improvement.

Example 1

(Preparation of Modified MpGDHs and Evaluation of Thermal Stability)

In accordance with the method descried in the Experimental Example above, PCR was performed by using pYES2C-Mp (wild type) as the template plasmid and a combination of synthetic nucleotides of SEQ ID NO s shown in Tables 1 and 2. Then, *Escherichia coli* JM109 strain was transformed with vectors containing the amplified DNAs. Nucleotide sequencing of the DNAs encoding the MpGDH in the plasmid DNAs harbored in the grown colonies was carried out to obtain recombinant plasmids: pYES2C-Mp-A175C/N214C, pYES2C-Mp-S192P, pYES2C-Mp-I212L, pYES2C-Mp-A218H, pYES2C-Mp-I226T, pYES2C-Mp-I226N, pYES2C-Mp-I226S, pYES2C-Mp-I226A, pYES2C-Mp-I226C, pYES2C-Mp-I226V, pYES2C-Mp-G466D, pYES2C-Mp-G466E, pYES2C-Mp-G466R, pYES2C-Mp-G466K pYES2C-Mp-G466H, pYES2C-Mp-G466N, pYES2C-Mp-G466S, pYES2C-Mp-G466Q, pYES2C-Mp-G466T, pYES2C-Mp-G466C, pYES2C-Mp-G466A, pYES2C-Mp-G466Y, pYES2C-Mp-G466F, pYES2C-Mp-G466M, pYES2C-Mp-G466V, pYES2C-Mp-G466L, pYES2C-Mp-G466W, and pYES2C-Mp-G466I having the following substitutions, respectively: a substitution of alanine at the 175th position of the amino acid sequence of SEQ ID NO: 1 with cysteine, and asparagine at the 214th position thereof with cysteine; a substitution of serine at the 192nd position thereof with proline; a substitution of isoleucine at the 212th position thereof with leucine; a substitution of alanine at the 218th position thereof with histidine; a substitution of isoleucine at the 226th position thereof with threonine, asparagine, serine, alanine, cysteine or valine; and a substitution of glycine at the 466th position thereof with aspartic acid, glutamic acid, arginine, lysine, histidine, asparagine, serine, glutamine, threonine, cysteine, alanine, tyrosine, phenylalanine, methionine, valine, leucine, tryptophan or isoleucine.

Next, using the recombinant plasmids encoding the aforementioned modified MpGDHs having site-specific mutations introduced thereinto, namely pYES2C-Mp-A175C/N214C, pYES2C-Mp-S192P, pYES2C-Mp-I212L, pYES2C-Mp-A218H, pYES2C-Mp-I226T, pYES2C-Mp-I226N, pYES2C-Mp-I226S, pYES2C-Mp-I226A, pYES2C-Mp-I226C, pYES2C-Mp-I226V, pYES2C-Mp-G466D, pYES2C-Mp-G466E, pYES2C-Mp-G466R, pYES2C-Mp-G466K pYES2C-Mp-G466H, pYES2C-Mp-G466N, pYES2C-Mp-G466S, pYES2C-Mp-G466Q, pYES2C-Mp-G466T, pYES2C-Mp-G466C, pYES2C-Mp-G466A, pYES2C-Mp-G466Y, pYES2C-Mp-G466F, pYES2C-Mp-G466M, pYES2C-Mp-G466V, pYES2C-Mp-G466L, pYES2C-Mp-G466W, and pYES2C-Mp-G466I, INVSc1 strain was transformed in accordance with Experimental Example, Section (2) and the resultant transformants (Sc-Mp-A175C/N214C strain. Sc-Mp-S192P strain, Sc-Mp-I212L strain, Sc-Mp-A218H strain, Sc-Mp-I226T strain, Sc-Mp-I226N strain, Sc-Mp-I226S strain, Sc-Mp-I226A strain, Sc-Mp-I226C strain, Sc-Mp-I226V strain, Sc-Mp-G466D strain, Sc-Mp-G466E strain, Sc-Mp-G466R strain, Sc-Mp-G466K strain, Sc-Mp-G466H strain, Sc-Mp-G466N strain, Sc-Mp-G466S strain, Sc-Mp-G466Q strain, Sc-Mp-G466T strain, Sc-Mp-G466C strain, Sc-Mp-G466A strain. Sc-Mp-G466Y strain, Sc-Mp-G466F strain, Sc-Mp-G466M strain, Sc-Mp-G466V strain, Sc-Mp-G466L strain, Sc-Mp-G466W strain, Sc-Mp-G466I strain) were cultured and the GDH activities of the culture supernatants were measured.

Subsequently, using the culture supernatants of the above mutants whose GDH activity was confirmed, and based on the procedures of Experimental Example, Sections (2) and (3) above, the residual activity ratio (%) after a heat treatment at 45° C. for 15 minutes, and the ratio of the reactivity to maltose relative to the reactivity to D-glucose (Mal/Glc (%) were determined and then, the Mal/Glc ratios (%) of the mutants were calculated based on taking the Mal/Glc (%) of the wild type as 100. The heat treatment at 40° C. was carried out by setting the heating time such that the residual activity ratio of the wild type became 25% or less such that difference in performance between the wild type and the mutants can readily be observed. The mutants were evaluated in the same conditions.

Incidentally, for example, "A175C" in Table 1 means (indicates) that A (Ala) of the 175th position is substituted with C (Cys). Further, e.g., "A175C/N214C" means that A (Ala) at the 175th position is substituted with C (Cys) and N (Asn) at the 214th position is substituted with C (Cys) and "/" means that both substitutions are present.

TABLE 1

| Recombinant plasmid | Primer SEQ ID NO | Residual activity ratio (%) at 40° C. | Residual activity ratio (%) at 45° C., 15 minutes | Mal/Glc ratio (%) |
|---|---|---|---|---|
| pYES2C-Mp (Wild type, Comparative Example) | — | 21 | 0 | 100 |
| pYES2C-Mp-A175C/N214C (Present Invention) | 5, 6, 7, 8 | — | 86 | 96 |
| pYES2C-Mp-S192P (Present Invention) | 34, 35 | 48 | — | 90 |
| pYES2C-Mp-I212L (Present Invention) | 36, 37 | 36 | — | 99 |
| pYES2C-Mp-A218H (Present Invention) | 39, 40 | 33 | — | 94 |
| pYES2C-Mp-I226T (Present Invention) | 41, 42 | 80 | — | 108 |
| pYES2C-Mp-I226N (Present Invention) | 42, 43 | 67 | — | 92 |
| pYES2C-Mp-I226S (Present Invention) | 42, 44 | 76 | — | 86 |
| pYES2C-Mp-I226A (Present Invention) | 42, 45 | 72 | — | 68 |
| pYES2C-Mp-I226C (Present Invention) | 42, 46 | 80 | — | 61 |
| pYES2C-Mp-I226V (Present Invention) | 42, 47 | 40 | — | 83 |

TABLE 2

| Recombinant plasmid | Primer SEQ ID NO | Mal/Glc ratio (%) |
|---|---|---|
| pYES2C-Mp (Wild type, Comparative Example) | — | 100 |
| pYES2C-Mp-G466D (Present Invention) | 9, 10 | 61 |
| pYES2C-Mp-G466E (Present Invention) | 10, 11 | 88 |
| pYES2C-Mp-G466R (Present Invention) | 10, 12 | 54 |
| pYES2C-Mp-G466K (Present Invention) | 10, 13 | 49 |
| pYES2C-Mp-G466N (Present Invention) | 10, 14 | 83 |
| pYES2C-Mp-G466Q (Present Invention) | 10, 15 | 68 |
| pYES2C-Mp-G466T (Present Invention) | 10, 16 | 77 |
| pYES2C-Mp-G466C (Present Invention) | 10, 17 | 49 |
| pYES2C-Mp-G466A (Present Invention) | 10, 18 | 84 |
| pYES2C-Mp-G466Y (Present Invention) | 10, 19 | 72 |
| pYES2C-Mp-G466F (Present Invention) | 10, 20 | 72 |
| pYES2C-Mp-G466M (Present Invention) | 10, 21 | 74 |
| pYES2C-Mp-G466V (Present Invention) | 10, 22 | 94 |
| pYES2C-Mp-G466L (Present Invention) | 10, 23 | 81 |
| pYES2C-Mp-G466W (Present Invention) | 10, 24 | 81 |
| pYES2C-Mp-G466S (Present Invention) | 10, 25 | 83 |
| pYES20-Mp-G466H (Present Invention) | 10, 26 | 83 |
| pYES2C-Mp-G466I (Present Invention) | 10, 27 | 81 |

As shown in Table 1, it was confirmed that the heat resistance of FAD-GDH is improved by introducing site-specific mutations into the wild type MpGDH at the 175th and 214th positions of SEQ ID NO: 1, more specifically, site-specific mutations of A175C/N214C. It was also confirmed that the heat resistance of FAD-GDH is improved by introducing a site-specific mutation into the wild type MpGDH at the 192nd, 212th, 218th and 226th positions of SEQ ID NO: 1, more specifically, the site-specific mutations of S192P, I212L, A218H, I226T, I226N, I226S, I226A, I226C, I226V.

Further, it was found that these FAD-GDHs having improved thermal stability maintain high substrate specificity. More specifically, it was found that the modified enzymes having a mutation for improving thermal stability of the present invention described in Table 1 may include modified enzymes having relatively higher substrate specificity than the wild type enzyme without virtually exerting a negative effect on the substrate specificity that wild type FAD-GDH has.

As shown in Table 2, it was confirmed that the Mal/Glc (%) of FAD-GDH is reduced by introducing a site-specific mutation into wild type MpGDH at the 466th position, more specifically, a site-specific mutation of G466D, G466E, G466R, G466K, G466N, G466Q, G466T, G466C, G466A, G466Y, G466F, G466M, G466V, G466L, G466W, G466S, G466H, and G466I.

Example 2

(Study on Combination Introduction of Mutations)

Mutants each having a plurality of mutations as shown in Example 2 were prepared and effects of improving thermal stability and substrate specificity were checked. More specifically, PCR was performed using pYES2C-Mp-A175C/N214C as the template plasmid and each of the combinations of synthetic nucleotides represented by the SEQ ID NOs in Table 2, and in accordance with the method described in the Experimental Example above. Then, Escherichia coli JM109 strain was transformed with a vector containing the amplified DNA. Nucleotide sequencing of the DNA encoding the MpGDH in the plasmid DNA that the grown colonies harbor was carried out to obtain the following multiple mutants characterized in that alanine at the 175th position was substituted with cysteine and asparagine at the 214th position with cysteine, and another amino acid substitution is present. More specifically, a recombinant plasmid, pYES2C-Mp-A75C/N214C/G466D encoding a triple mutant having a substitution of alanine at the 175th position of the amino acid sequence of SEQ ID NO: 1 with cysteine; a substitution of asparagine at the 214th position thereof with cysteine; and a substitution of glycine at the 466th position thereof with glutamic acid, was obtained.

Subsequently, using a recombinant plasmid encoding a modified MpGDH having site-specific mutations introduced thereinto (pYES2C-Mp-A175C/N214C/G466D) and in accordance with Experimental Example, Section (2), INVSc1 strain was transformed and the obtained transformant (Sc-Mp-A175C/N214C/G466D strain) was cultured and the GDH activity of the culture supernatant was measured.

Subsequently, using the culture supernatants of the multiple mutants whose GDH activity was confirmed, the residual activity ratio (%) after a heat treatment at 45° C. for 15 minutes and the ratio (Mal/Glc (%)), which is the ratio of the reactivity to maltose relative to the reactivity to D-glucose, were determined in accordance with the procedures of Experimental Example, Sections (2) and (3).

TABLE 3

| Recombinant plasmid | Primer SEQ ID NO | Residual activity ratio (%) 45° C. | Mal/Glc ratio (%) |
|---|---|---|---|
| pYES2C-Mp (Wild type, Comparative Example) | — | 0 | 100 |
| pYES2C-Mp-A17C/N214C/G466D (Present Invention) | 9, 10 | 37 | 56 |

As shown in Table 3, it was confirmed that thermal stability higher than that of the wild type is maintained and Mal/Glc (%) is reduced by introducing A175C/N214C into the amino acid sequence of SEQ ID NO: 1 in combination with the amino acid substitution G466D.

Example 3

A gene encoding a modified GDH (hereinafter also referred to as MpGDH-M1) was obtained by introducing mutations of N66Y/N68G/C88A/Q233R/T387C/E554D/L557V/S559K into a Mucor-derived GDH (MpGDH, SEQ ID NO: i). The amino acid sequence of MpGDH-M1 is shown in SEQ ID NO: 3 and the nucleotide sequence of the gene thereof is shown in SEQ ID NO: 4. It was examined whether mutations for improvement of thermal stability and substrate specificity provided in Examples 1 and 2 are effective for MpGDH-M1.

PCR was performed in the same manner as in Examples 1 and 2, using pYES2C-MpGDH-M1 as the template plasmid and combinations of synthetic nucleotides of the SEQ ID NOs described in Tables 4 and 5. Then, *Escherichia coli* JM109 strain was transformed with a vector containing the amplified DNA. Nucleotide sequencing of the DNA encoding the MpGDH in the plasmid DNA that the grown colonies harbor was carried out to prepare a recombinant plasmid, pYES2C-MpGDH-M1-A175C/N214C, encoding a multiple mutant in which alanine at the 175th position is substituted with cysteine and asparagine at the 214th position is substituted with cysteine. Further, recombinant plasmids pYES2C-MpGDH-M1-G466D, pYES2C-MpGDH-M1-G466E, pYES2C-MpGDH-M1-G466R, pYES2C-MpGDH-M1-G466K, pYES2C-MpGDH-M1-G466H, pYES2C-MpGDH-M1-G466N, and pYES2C-MpGDH-M 1-G466S encoding mutants where glycine at the 466th position is substituted with aspartic acid, glutamic acid, arginine, lysine, histidine, asparagine and serine, were prepared. Further, a recombinant plasmid, pYES2C-MpGDH-M1-A175C/N214C/G466D encoding a multiple mutant where alanine at the 175th position is substituted with cysteine and asparagine at the 214th position is substituted with cysteine and glycine at the 466th position is substituted with aspartic acid, was prepared.

Further, PCR was performed using recombinant plasmid pYES2C-MpGDH-M1-A175C/N214C/G466D as the template plasmid and the combinations of synthetic nucleotides of the SEQ ID NOs described in Tables 4 and 5. As a result, recombinant plasmids pYES2C-MpGDH-M 1-A175C/N214C/G466D/S192P, pYES2C-MpGDH-M1-A175C/N214C/G466D/I212L, pYES2C-MpGDH-M1-A175C/N214C/G466D/I212M, pYES2C-MpGDH-M1-A175C/N214C/G466D/A218H, pYES2C-MpGDH-M1-A175C/N214C/G466D/I226T, pYES2C-MpGDH-M1-A175C/N214C/G466D/I226N, pYES2C-MpGDH-M1-A175C/N214C/G466D, I226S, pYES2C-MpGDH-M1-A175C/N214C/G466D/I226A, pYES2C-MpGDH-M1-A175C, N214C/G466D/I226C, and pYES2C-MpGDH-M1-A175C/N214C/G466D/I226V encoding mutants where serine at the 192nd position is substituted with proline; isoleucine at the 212th position is substituted with leucine or methionine; alanine at the 218th position is substituted with histidine; and isoleucine at the 226th position is substituted with threonine, asparagine, serine, alanine, cysteine or valine were obtained. Further, PCR was performed using recombinant plasmids pYES2C-MpGDH-M1-A175C/N214C/G466D/I212L, pYES2C-MpGDH-M1-A175C/N214C/G466D, I212M as the template plasmid and the combinations of synthetic nucleotides of the SEQ ID NOs described in Table 4. As a result, recombinant plasmids pYES2C-MpGDH-M1-A175C/N214C/G466D/I212L/A218H, and pYES2C-MpGDH-M1-A175C/N214C/G466D/I212M/A218H encoding mutants where alanine at the 218th position is substituted with histidine were obtained.

Then, using recombinant plasmids encoding the modified MpGDH-M1 having site-specific mutations introduced thereinto, INVSc1 strain was transformed in accordance with Experimental Example, Section (2). The obtained transformants (Sc-MpGDH-M1-A175C/N214C strain, Sc-MpGDH-M1-A175C/N214C/G466D/S192P strain, Sc-MpGDH-M1-A175C/N214C/G466D/I212L strain, Sc-MpGDH-M1-A175C/N214C/G466D/I212M strain, Sc-MpGDH-M1-A175C/N214C/G466D/A218H strain, Sc-MpGDH-M1-A175C/N214C/G466D/I226T strain, Sc-MpGDH-M1-A175C/N214C/G466D/I226N strain, Sc-MpGDH-M1-A175C/N214C/G466D/I226S strain. Sc-MpGDH-M1-A175C/N214C/G466D/I226A strain, Sc-MpGDH-M1-A175C/N214C/G466D/I226C strain. Sc-MpGDH-M1-A175C/N214C/G466D/I226V strain, Sc-MpGDH-M1-A175C/N214C/G466D/I212L/A218H strain, Sc-MpGDH-M1-A175C/N214C/G466D/I212M/A218H strain, Sc-MpGDH-M1-G466D strain, Sc-MpGDH-M1-G466E strain, Sc-MpGDH-M1-G466R strain, Sc-MpGDH-M1-G466K strain, Sc-MpGDH-M-G466H strain, Sc-MpGDH-M1-G466N strain, Sc-MpGDH-M1-G466S strain, and Sc-MpGDH-M1-A175C/N214C/G466D strain) were cultured and the GDH activities of the culture supernatants were measured.

Subsequently, using the culture supernatants of the multiple mutants above whose GDH activity was confirmed, the residual activity ratio (%) after a heat treatment at 50° C. for 15 minutes; the residual activity ratio (%) after a heat treatment at 55° C. for 15 minutes; and the residual activity ratio (%) after a heat treatment at 60° C. for 15 minutes, and the ratio (Mal/Glc (%)), which is the ratio of the reactivity to maltose relative to the reactivity to D-glucose, were determined in accordance with the procedures of Experimental Example, Sections (2) and (3).

TABLE 4

| Recombinant plasmid | Template plasmid | Primer SEQ ID NO | Residual activity ratio (%) 50° C. | 55° C. | 60° C. | Mal/Glc (%) |
|---|---|---|---|---|---|---|
| pYES2C-MpGDH-M1 (Comparative Example) | — | — | 56 | 1.7 | — | 0.88 |
| pYES2C-MpGDH-M1-A175C/N214C (Present Invention) | pYES2C-MpGDH-M1 | 5, 6, 7, 8 | 97 | 90 | — | 0.80 |
| pYES2C-MpGDH-M1-A175C/N214C/G466D (Present Invention) | pYES2C-MpGDH-M1-A175C/N214C | 9, 10 | — | 66 | 2.1 | 0.55 |
| pYES2C-MpGDH-M1-A175C/N214C/G466D/S192P (Present Invention) | pYES2C-MpGDH-M1-A175C/N214C/G466D | 34, 35 | — | — | 26 | 0.59 |
| pYES2C-MpGDH-M1-A175C/N214C/G466D/I212L (Present Invention) | pYES2C-MpGDH-M1-A175C/N214C/G466D | 48, 49 | — | — | 33 | 0.53 |
| pYES2C-MpGDH-M1-A175C/N214C/G466D/I212M (Present Invention) | pYES2C-MpGDH-M1-A175C/N214C/G466D | 49, 50 | — | 72 | — | 0.40 |

TABLE 4-continued

| Recombinant plasmid | Template plasmid | Primer SEQ ID NO | Residual activity ratio (%) 50° C. | 55° C. | 60° C. | Mal/Glc (%) |
|---|---|---|---|---|---|---|
| pYES2C-MpGDH-M1-A175C/N214C/G466D/A218H (Present Invention) | pYES2C-MpGDH-M1-A175C/N214C/G466D | 39, 40 | — | — | 13 | 0.54 |
| pYES2C-MpGDH-M1-A175C/N214C/G466D/I212L/A218H (Present Invention) | pYES2C-MpGDH-M1-A175C/N214C/G466D/I212L | 39, 40 | — | — | 47 | 0.60 |
| pYES2C-MpGDH-M1-A175C/N214C/G466D/I212M/A218H (Present Invention) | pYES2C-MpGDH-M1-A175C/N214C/G466D/I212M | 39, 40 | — | — | 20 | 0.55 |
| pYES2C-MpGDH-M1-A175C/N214C/G466D/I226T (Present Invention) | pYES2C-MpGDH-M1-A175C/N214C/G466D | 41, 51 | — | — | 66 | 0.63 |
| pYES2C-MpGDH-M1-A175C/N214C/G466D/I226N (Present Invention) | pYES2C-MpGDH-M1-A175C/N214C/G466D | 51, 43 | — | — | 19 | 0.63 |
| pYES2C-MpGDH-M1-A175C/N214C/G466D/I226S (Present Invention) | pYES2C-MpGDH-M1-A175C/N214C/G466D | 84, 87 | — | 90 | 56 | 0.39 |
| pYES2C-MpGDH-M1-A175C/N214C/G466D/I226A (Present Invention) | pYES2C-MpGDH-M1-A175C/N214C/G466D | 85, 87 | — | 92 | 54 | 0.44 |
| pYES2C-MpGDH-M1-A175C/N214C/G466D/I226C (Present Invention) | pYES2C-MpGDH-M1-A175C/N214C/G466D | 86, 87 | — | 89 | 45 | 0.35 |
| pYES2C-MpGDH-M1-A175C/N214C/G466D/I226V (Present Invention) | pYES2C-MpGDH-M1-A175C/N214C/G466D | 51, 47 | — | — | 6.5 | 0.64 |

TABLE 5

| Recombinant plasmid | Primer SEQ ID NO | Mal/Glc (%) |
|---|---|---|
| pYES2C-MpGDH-M1 (Comparative Example) | — | 0.88 |
| pYES2C-MpGDH-M1-G466D (Present Invention) | 9, 10 | 0.50 |
| pYES2C-MpGDH-M1-G466E (Present Invention) | 10, 11 | 0.74 |
| pYES2C-MpGDF-M1-G466R (Present Invention) | 10, 12 | 0.64 |
| pYES2C-MpGDH-M1-G466K (Present Invention) | 10, 13 | 0.54 |
| pYES2C-MpGDH-M1-G466H (Present Invention) | 10, 26 | 0.76 |
| pYES2C-MpGDH-M1-G466N (Present Invention) | 10, 14 | 0.67 |
| pYES2C-MpGDH-M1-G466S (Present Invention) | 10, 25 | 0.74 |

As shown in Table 4, it was confirmed that the heat resistance of FAD-GDH is improved by introducing site-specific mutations into MpGDH-M1 of SEQ ID NO: 3 at the 175th and 214th positions, more specifically site-specific mutations of A175C/N214C. It was also found that the reactivity to maltose is reduced by introducing site-specific mutations of A175C/N214C. It was further confirmed that the heat resistance of FAD-GDH is further improved by introducing site-specific mutations into the multiple mutant in which site-specific mutations of A175C/N214C/G466D is introduced into MpGDH-M1 of SEQ ID NO: 3, at 192nd, 212th, 218th and 226th positions, more specifically, site-specific mutations of S192P, I212L, I212M, A218H, I226T, I226N, I226S, I226A, I226C, and I226V.

As shown in Table 5, it was confirmed that the Mal/Glc (%) of FAD-GDH is reduced by introducing a site-specific mutation into MpGDH-M1 of SEQ ID NO: 3 at the 466th position, more specifically a site-specific mutation of G466D, G466E. G466R, G466K, G466H, G466N, and G466S.

Example 4

(Preparation of Various Modified MgGDHs and Evaluation of Thermal Stability and Substrate Specificity)

JP Patent Publication (Kokai) No. 2017-000137 discloses the sequence information of GDH from *Mucor guilliermondii* of SEQ ID NO: 28 (hereinafter referred to as MgGDH) and having an identity of 78% with MpGDH. Whether thermal stability is improved or the reactivity to maltose is reduced by introducing the amino acid substitutions found in Example 1 into MgGDH was tested as follows.

The amino acid sequence of MgGDH is shown in SEQ ID NO: 28 and the nucleotide sequence of the gene thereof is shown in SEQ ID NO: 29. In the same manner as in Example 1, PCR was performed by using synthetic oligonucleotides of SEQ ID NO: 52, 53, 54, 55 to obtain DNA constructs encoding a mutant, MgGDH/T170C/N209C. obtained by substituting threonine of the 170th position of the amino acid sequence of SEQ ID NO: 28 with cysteine and asparagine at the 209th position thereof with cysteine; and mutants MgGDH/I221T and MgGDH/I221S, obtained by substituting isoleucine at the 221st position with threonine and serine, respectively; and a mutant. MgGDH/S213H obtained by substituting serine at the 213th position with histidine. Subsequently, genes of interest were prepared using the primers described in Table 6 and in the same manner as in Example 1. Using recombinant plasmids pYES2C-Mg, pYES2C-Mg-T170C/N209C, pYES2C-Mg-I221T, pYES2C-Mg-I221S, and pYES2C-Mg-S213H in which genes encoding MgGDH as well as MgGDH/T170C/N209C, MgGDH/I221T, MgGDH/I221S, and MgGDH/S213H were inserted, INVSc1 strain was transformed in accordance with Experimental Example, Section (2) and the obtained transformants (Sc-MpGDH-Mg strain, Sc-MpGDH-Mg-T170C/N209C strain, Sc-MpGDH-Mg-I221T strain, Sc-MpGDH-Mg-I221S strain, Sc-MpGDH-Mg-S213H strain) were cultured and the GDH activities of the culture supernatants were measured. Genes of interest were prepared in a similar manner using the primers described in Table 7. Using mutants MgGDH/G461D, MgGDH/G461R, MgGDH/G461K, MgGDH/G461H, and MgGDH/G461S obtained by substituting glycine at the 461st position of the amino acid sequence of SEQ ID NO: 28 with aspartic acid, arginine, lysine, histidine and serine, transformation was performed and the obtained transformants were cultured, and then, the GDH activities of the culture supernatants were measured.

Subsequently, using the culture supernatants of the multiple mutants above whose GDH activity was confirmed, the residual activity ratio (%) after a heat treatment at 40° C. for 15 minutes; the residual activity ratio (O %) after a heat treatment at 55° C. for 15 minutes; and the ratio (Mal/Glc (%)), which is the ratio of the reactivity to maltose relative to the reactivity to D-glucose, were determined in accordance with the procedures of Experimental Example, Sections (2) and (3).

TABLE 6

| Recombinant plasmid | Primer SEQ ID NO | Residual activity ratio (%) 40° C. | Residual activity ratio (%) 55° C. |
|---|---|---|---|
| pYES2C-Mg (Comparative Example) | — | 40.7 | 0.3 |
| pYES2C-Mg-T170C/N209C (Present Invention) | 52, 53, 54, 55 | — | 76.4 |
| pYES2C-Mg-I221T (Present Invention) | 56, 57 | 75.6 | — |
| pYES2C-Mg-I221S (Present Invention) | 57, 91 | 44.7 | — |
| pYES2C-Mg-S213H (Present Invention) | 92, 93 | 42.1 | — |

TABLE 7

| Recombinant plasmid | Primer SEQ ID NO | Mal/Glc (%) |
|---|---|---|
| pYES2C-Mg (Comparative Example) | — | 9.8 |
| pYES2C-Mg-G461D (Present Invention) | 66, 67 | 6.2 |
| pYES2C-Mg-G461R (Present Invention) | 67, 68 | 2.9 |
| pYES2C-Mg-G461K (Present Invention) | 67, 69 | 9.1 |
| pYES2C-Mg-G461H (Present Invention) | 67, 70 | 1.4 |
| pYES2C-Mg-G461S (Present Invention) | 67, 71 | 3.3 |

As shown in Table 6, it was confirmed that the heat resistance of FAD-GDH is improved by introducing site-specific mutations into MgGDH of SEQ ID NO: 28 at the 170th and 209th positions, more specifically, site-specific mutations of T170C/N209C. It was also confirmed that the heat resistance of FAD-GDH is improved by introducing site-specific mutations into MgGDH of SEQ ID NO: 28 at the 221st and 213th positions, more specifically, site-specific mutations of I221 T, I221S and S213H.

As shown in Table 7, it was confirmed that the Mal/Glc (%) of FAD-GDH is reduced by introducing a site-specific mutation into MgGDH of SEQ ID NO: 28 at the 461st position, more specifically, the site-specific mutations of G461D, G461R, G461K, G461H or G461S.

Example 5

(Preparation of Various Modified MhGDHs and Evaluation of Thermal Stability and Substrate Specificity)

JP Patent Publication (Kokai) No. 2013-116102 discloses the sequence information of GDH derived from Mucor hiemalis of SEQ ID NO: 30 (hereinafter referred to as MhGDH) and having an identity of 78% with MpGDH. Whether thermal stability is improved or the reactivity to maltose is reduced as well by introducing the amino acid substitutions found in Example 1 into MhGDH was tested as follows.

The amino acid sequence of MhGDH is represented by SEQ ID NO: 30 and the nucleotide sequence of the gene thereof is represented by SEQ ID NO: 31. In the same manner as in Example 1, PCR was performed by using synthetic oligonucleotides of SEQ ID NO: 58, 59, 60, 61 to obtain a DNA construct encoding a mutant, MhGDH/V172C/N211C obtained by substituting valine at the 172nd position of the amino acid sequence of SEQ ID NO: 30 with cysteine and asparagine at the 211th position thereof with cysteine. Subsequently, in the same manner as in Example 1, using recombinant plasmids (pYES2C-Mh, pYES2C-Mh-V172C/N211C) having genes encoding MhGDH and MhGDH/V172C/N211C inserted, respectively, INVSc1 strain was transformed in accordance with Experimental Example. Section (2) and the obtained transformants (Sc-MpGDH-Mh strain. Sc-MpGDH-Mh-V172C/N211C strain) were cultured and the GDH activities of the culture supernatants were measured. Genes of interest were prepared in a similar manner using the primers described in Table 9. Mutants MhGDH/G463D, MhGDH/G463R, MhGDH/G463K, MhGDH/G463H, and MhGDH/G463S obtained by substituting glycine at the 463rd position of the amino acid sequence of SEQ ID NO:30 with aspartic acid, arginine, lysine, histidine and serine were used for transformation and the obtained transformants were cultured, and then, the GDH activities of the culture supernatants were measured.

Subsequently, using the culture supernatants of the above multiple mutants whose GDH activity was confirmed, the residual activity ratio (%) after a heat treatment at 55° C. for 15 minutes; and the ratio (Mal/Glc (%)), which is the ratio of the reactivity to maltose relative to the reactivity to D-glucose, were determined in accordance with the procedures of Experimental Example, Sections (2) and (3).

TABLE 8

| Recombinant plasmid | Primer SEQ ID NO | Residual activity ratio (%) 55° C. |
|---|---|---|
| pYES2C-Mh (Comparative Example) | — | 9.0 |
| pYES2C-Mh-V172C/N211C (Present Invention) | 58, 59, 60, 61 | 61 |

TABLE 9

| Recombinant plasmid | Primer SEQ ID NO | Mal/Glc (%) |
| --- | --- | --- |
| pYES2C-Mh (Comparative Example) | | 6.6 |
| pYES2C-Mh-G463D (Present invention) | 72, 73 | 4.4 |
| pYES2C-Mh-G463R (Present invention) | 73, 74 | 4.0 |
| pYES2C-Mh-G463K (Present Invention) | 73, 75 | 3.5 |
| pYES2C-Mh-G463H (Present Invention) | 73, 76 | 3.2 |
| pYES2C-Mh-G463S (Present Invention) | 73, 77 | 5.5 |

As shown in Table 8, it was confirmed that the heat resistance of FAD-GDH is improved by introducing site-specific mutations into MhGDH of SEQ ID NO: 30 at the 172nd and 211th positions, more specifically, site-specific mutations of V172C/N211C.

As shown in Table 9, it was confirmed that the Mal/Glc (%) of FAD-GDH is reduced by introducing a site-specific mutation into MhGDH of SEQ ID NO: 30 at the 463rd position, more specifically, the site-specific mutations of G463D, G463R, G463K, G463H or G463S.

Example 6

(Preparation of Various Modified MrdGDHs and Evaluation of Substrate Specificity)

JP Patent Publication (Kokai) No. 2013-176363 discloses the sequence information of GDH derived from *Mucor* RD056860 of SEQ ID NO: 32 (hereinafter referred to as MrdGDH) and having an identity of 73% with MpGDH. Whether thermal stability is improved or the reactivity to maltose is reduced by introducing the amino acid substitutions found in Example 1 to MrdGDH, was tested as follows.

The amino acid sequence of MrdGDH is shown in SEQ ID NO: 32 and the nucleotide sequence of the gene thereof is shown in SEQ ID NO: 33. In the same manner as in Example 1. PCR was performed by using synthetic oligonucleotides of SEQ ID NO: 62, 63, 64, 65 to obtain a DNA construct encoding a mutant, MrdGDH/V171C/D210C obtained by substituting valine at the 171st position of the amino acid sequence of SEQ ID NO: 32 with cysteine and aspartic acid at the 210th position thereof with cysteine. Subsequently, in the same manner as in Example 1, using recombinant plasmids pYES2C-Mrd, and pYES2C-Mrd-V171C/D210C in which genes encoding MrdGDH and MrdGDH/V171C/D210C were inserted, respectively, INVSc1 strain was transformed in accordance with Experimental Example, Section (2) and the obtained transformants (Sc-Mrd strain, Sc-Mrd-V171C/D210C strain) were cultured and the GDH activities of the culture supernatants were measured. Genes of interest were prepared in a similar manner using the primers described in Table 11. Mutants MrdGDH/G463D, MrdGDH/G463C, MrdGDH/G463R, MrdGDH, G463K, MrdGDH/G463H, MrdGDH/G463N, and MrdGDH/G463S obtained by substituting glycine at the 463rd position of the amino acid sequence of SEQ ID NO:32 with aspartic acid, cysteine, arginine, lysine, histidine, asparagine and serine, were used for transformation and the transformants obtained were cultured, and then, the GDH activities of the culture supernatants were measured.

Subsequently, using the culture supernatants of the above multiple mutants whose GDH activity was confirmed, the residual activity ratio (%) after a heat treatment at 55° C. for 15 minutes; and the ratio (Mal/Glc (%)), which is the ratio of the reactivity to maltose relative to the reactivity to D-glucose, were determined in accordance with the procedures of Experimental Example. Sections (2) and (3)

TABLE 10

| Recombinant plasmid | Primer SEQ ID NO | Residual activity ratio (%) 55° C. |
| --- | --- | --- |
| pYES2C-Mrd (Comparative Example) | — | 2.1 |
| pYES2C-Mrd-V171C/D210C (Present Invention) | 62, 63, 64, 65 | 98 |

TABLE 11

| Recombinant plasmid | Primer SEQ ID NO | Mal/Glc (%) |
| --- | --- | --- |
| pYES2C-Mrd (Comparative Example) | — | 7.2 |
| pYES2C-Mrd-G463D (Present Invention) | 78, 79 | 1.8 |
| pYES2C-Mrd-G463C (Present Invention) | 88, 89 | 2.6 |
| pYES2C-Mrd-G463R (Present Invention) | 79, 80 | 1.3 |
| pYES2C-Mrd-G463K (Present Invention) | 79, 81 | 1.5 |
| pYES2C-Mrd-G463H (Present Invention) | 79, 82 | 2.0 |
| pYES2C-Mrd-G463N (Present Invention) | 89, 90 | 4.1 |
| pYES2C-Mrd-G463S (Present Invention) | 79, 83 | 4.2 |

As shown in Table 10, it was confirmed that the heat resistance of FAD-GDH is improved by introducing site-specific mutations into MrdGDH of SEQ ID NO: 32 at the 171st and 210th positions thereof, more specifically, site-specific mutations of V171C/D210C.

As shown in Table 11, it was confirmed that the Mal/Glc (%) of FAD-GDH is reduced by introducing a site-specific mutation into MrdGDH of SEQ ID NO: 32 at the 463rd position, more specifically, the site-specific mutation of G463D, G463C, G463R, G463K, G463H, G463N or G463S.

As described in the above, the FAD-GDH of the present invention has excellent thermal stability and sufficiently high substrate specificity to D-glucose and, therefore, even when D-glucose in the sample is measured under conditions where sugar compounds other than D-glucose such as maltose are present in large amounts and under conditions where the enzyme concentration is high, the concentration of D-glucose can be accurately measured. For example, it is expected that when the FAD-GDH of the present invention is applied to a glucose sensor and the like, more accurate and sensitive measurement is possible compared to cases where conventional FAD-GDHs are used. Furthermore, when producing sensor chips, it is expected that reduction of activity due to heat can be suppressed regarding the FAD-GDH of the present invention compared to cases where conventional FAD-GDHs are used, and this can contribute to long-term stability of the sensor chip.

The invention claimed is:

1. An electrode comprising a modified glucose dehydrogenase using a flavin adenine dinucleotide (FAD) as a coenzyme (FAD-GDH), wherein the modified FAD-GDH is based on a FAD-GDH before amino acid substitution selected from the group consisting of (i) to (iv):

(i) FAD-GDH comprising an amino acid sequence having an identity of 85% or more with the amino acid sequence of SEQ ID NO: 1 and having glucose dehydrogenase activity;

(ii) FAD-GDH comprising an amino acid sequence having an identity of 85% or more with the amino acid sequence of SEQ ID NO: 1 over the full length and having an identity of 90% or higher identity between the homologous region consisting of positions 31 to 41, 58 to 62, 71 to 85, 106 to 116, 119 to 127, 132 to 134, 136 to 144, 150 to 153, 167 to 171, 219 to 225, 253 to 262, 277 to 281, 301 to 303, 305 to 312, 314 to 319, 324 to 326, 332 to 337, 339 to 346, 348 to 354, 386 to 394, 415 to 417, 454 to 459, 476 to 484, 486 to 491, 508 to 511, 518 to 520, 522 to 524, 526 to 528, 564 to 579, 584 to 586, 592 to 595, 597 to 599, 607 to 617 and 625 to 630 of SEQ ID NO: 1 and the homologous region of the FAD-GDH consisting of corresponding positions and having glucose dehydrogenase activity;

(iii) FAD-GDH comprising an amino acid sequence having an identity of 85% or more with the amino acid sequence of SEQ ID NO: 1 over the full length and having an identity of 95% or higher identity between the homologous region consisting of positions 31 to 41, 58 to 62, 71 to 85, 106 to 116, 119 to 127, 132 to 134, 136 to 144, 150 to 153, 167 to 171, 219 to 225, 253 to 262, 277 to 281, 301 to 303, 305 to 312, 314 to 319, 324 to 326, 332 to 337, 339 to 346, 348 to 354, 386 to 394, 415 to 417, 454 to 459, 476 to 484, 486 to 491, 508 to 511, 518 to 520, 522 to 524, 526 to 528, 564 to 579, 584 to 586, 592 to 595, 597 to 599, 607 to 617 and 625 to 630 of SEQ ID NO: 1 and the homologous region of the FAD-GDH consisting of corresponding positions and having glucose dehydrogenase activity; and (iv) FAD-GDH comprising an amino acid sequence having an identity of 90% or more with the amino acid sequence of SEQ ID NO: 1 over the full length and having glucose dehydrogenase activity;

and wherein the modified FAD-GDH comprises an amino acid substitution at the position(s) corresponding to the following amino acid(s):

the amino acid at the 175th position in the amino acid sequence of SEQ ID NO: 1 is cysteine, and the amino acid at the 214th position in the amino acid sequence of SEQ ID NO: 1 is cysteine; and has an improved thermal stability compared to the FAD-GDH before the amino acid substitution.

2. The electrode of claim 1, wherein the modified FAD-GDH further comprises an amino acid substitution at the position(s) corresponding to the following amino acid(s):

the amino acid at the position corresponding to the 192nd position in the amino acid sequence of SEQ ID NO: 1 is proline, the amino acid at the position corresponding to the 212th position in the amino acid sequence of SEQ ID NO: 1 is leucine or methionine, the amino acid at the position corresponding to the 218th position in the amino acid sequence of SEQ ID NO: 1 is histidine, and/or the amino acid at the position corresponding to the 226th position in the amino acid sequence of SEQ ID NO: 1 is any one of threonine, asparagine, alanine, serine, cysteine and valine; and has an improved thermal stability compared to the FAD-GDH before the further amino acid substitution.

3. The electrode of claim 1, wherein the modified FAD-GDH comprises the following amino acid(s):

the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is aspartic acid, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is glutamic acid, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is arginine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is lysine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is histidine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is asparagine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is serine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is glutamine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is threonine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is cysteine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is alanine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is tyrosine;

the amino acid at the position corresponding to alanine at the 175th position in the amino acid sequence of SEQ ID NO: 1 is cysteine, the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is phenylalanine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is methionine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is valine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is leucine, the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is tryptophan, or the amino acid at the position corresponding to alanine at the 175th position in the amino acid sequence of SEQ ID NO: 1 is cysteine; the amino acid at the position corresponding to asparagine at the 214th position in the amino acid sequence of SEQ ID NO: 1 is cysteine; and the amino acid at the position corresponding to glycine at the 466th position in the amino acid sequence of SEQ ID NO: 1 is isoleucine.

4. A glucose sensor comprising the electrode of claim 1.

5. The electrode of claim 1, wherein the modified FAD-GDH of (i), (ii), (iii) and (iv) are each based on a FAD-GDH before amino acid substitution comprising an amino acid sequence having an identity of 95% or more with the amino acid sequence of SEQ ID NO: 1 over the full length and having glucose dehydrogenase activity.

6. A method for measuring glucose using the electrode of claim 1.

* * * * *

SEQUENCE LISTING

<160> NUMBER OF SEQ ID NOS: 97

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
                35                  40                  45

Arg Ile Ser Glu Asn Lys Asp Val Thr Val Ala Val Leu Glu Ser Gly
        50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

| | | | | | | | | | | | |
|---|---|---|---|---|---|---|---|---|---|---|---|
| Ala | Gln | Glu | Gln | Arg | Glu | Glu | Tyr | Glu | Ala | Asn | Lys | Thr | Gly | Ile | Trp |
| | 370 | | | | 375 | | | | 380 | | |

Ala Gln Glu Gln Arg Glu Glu Tyr Glu Ala Asn Lys Thr Gly Ile Trp
       370                      375                   380

Ala Thr Thr Pro Asn Asn Leu Gly Tyr Pro Thr Pro Glu Gln Leu Phe
385                      390                      395                  400

Asn Gly Thr Glu Phe Val Ser Gly Lys Glu Phe Ala Asp Lys Ile Arg
                 405                      410                   415

Asn Ser Thr Asp Glu Trp Ala Asn Tyr Tyr Ala Ser Thr Asn Ala Ser
         420                      425                  430

Asn Val Glu Leu Leu Lys Lys Gln Tyr Ala Ile Val Ala Ser Arg Tyr
              435                     440                   445

Glu Glu Asn Tyr Leu Ser Pro Ile Glu Ile Asn Phe Thr Pro Gly Tyr
450                     455                     460

Glu Gly Ser Gly Asn Val Asp Leu Gln Asn Asn Lys Tyr Gln Thr Val
465                     470                     475                  480

Asn His Val Leu Ile Ala Pro Leu Ser Arg Gly Tyr Thr His Ile Asn
              485                     490                   495

Ser Ser Asp Val Glu Asp His Ser Val Ile Asn Pro Gln Tyr Tyr Ser
         500                      505                  510

His Pro Met Asp Ile Asp Val His Ile Ala Ser Thr Lys Leu Ala Arg
              515                     520                   525

Glu Ile Ile Thr Ala Ser Pro Gly Leu Gly Asp Ile Asn Ser Gly Glu
530                     535                     540

Ile Glu Pro Gly Met Asn Ile Thr Ser Glu Asp Asp Leu Arg Ser Trp
545                     550                     555                  560

Leu Ser Asn Asn Val Arg Ser Asp Trp His Pro Val Gly Thr Cys Ala
                 565                     570                   575

Met Leu Pro Lys Glu Leu Gly Gly Val Val Ser Pro Ala Leu Met Val
             580                     585                   590

Tyr Gly Thr Ser Asn Leu Arg Val Val Asp Ala Ser Ile Met Pro Leu
         595                      600                  605

Glu Val Ser Ser His Leu Met Gln Pro Thr Tyr Gly Ile Ala Glu Lys
         610                      615                  620

Ala Ala Asp Ile Ile Lys Asn Phe Tyr Lys Thr Gln His Lys Asn Gln
625                     630                     635                  640

Asn

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct    60
caacaagaca caaattcttc ctcaactgat acttatgatt atgttatcgt tggcggcggt   120
gtagctggtt tggctttggc tagtcgtatc tctgaaaaca aggatgtcac tgttgctgtt   180
ctcgagtccg gtcctaatgc caatgataga tttgttgttt atgctcctgg catgtatggc   240
caagctgttg gcactgatct ctgtcctctc attcctacta ctcctcaaga aaatatgggc   300
aacagaagtc tcacaatcgc tactggtaga ttgctcggtg gtggcagtgc tattaatggt   360
ctcgtttgga cccgtggtgg cttgaaggat tacgatgctt gggaggagct cggtaaccct   420
ggatggaacg gtgccaactt gttcaagtac tttaagaagg tcgaaaactt cactcctcct   480
actcctgccc aaattgaata cggcgctact tatcagaaaa gtgctcatgg caagaaggga   540
```

```
cctattgatg tctctttcac gaactacgag ttctctcaat ctgctagctg gaacgcctca    600
ctcgaaaccc ttgatttcac tgcacttcct gatatcttga acggtacttt ggccggttac    660
tctaccactc ccaacatttt ggaccctgag actgttcaac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctactac tcccaacaac ctcggttatc ctacgcccga caactcttc    1200 aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc tatggatat tgatgtccat   1560 atcgcttcca ctaaacttgc tcgcgaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg tgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926
```

<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

```
Lys Asp Tyr Asp Ala Trp Glu Glu Leu Gly Asn Pro Gly Trp Asn Gly
            130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
530                 535                 540
```

| | | | | | | | | | | | |
|---|---|---|---|---|---|---|---|---|---|---|---|
|Ile|Glu|Pro|Gly|Met|Asn|Ile|Thr|Ser|Asp|Asp|Val|Arg|Lys|Trp|
|545| | | |550| | | |555| | | |560|

Leu Ser Asn Asn Val Arg Ser Asp Trp His Pro Val Gly Thr Cys Ala
              565                     570                    575

Met Leu Pro Lys Glu Leu Gly Gly Val Val Ser Pro Ala Leu Met Val
         580                     585                    590

Tyr Gly Thr Ser Asn Leu Arg Val Val Asp Ala Ser Ile Met Pro Leu
       595                   600                 605

Glu Val Ser Ser His Leu Met Gln Pro Thr Tyr Gly Ile Ala Glu Lys
     610                 615                620

Ala Ala Asp Ile Ile Lys Asn Phe Tyr Lys Thr Gln His Lys Asn Gln
625                 630                 635            640

Asn

<210> SEQ ID NO 4
<211> LENGTH: 1926
<212> TYPE: DNA
<213> ORGANISM: Mucor prainii

<400> SEQUENCE: 4

```
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtccttatgc cggtgataga tttgttgttt atgctcctgg catgtatggc     240
caagctgttg gcactgatct cgctcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg gtgccaactt gttcaagtac tttaagaagg tcgaaaactt cactcctcct     480
actcctgccc aaattgaata cggcgctact tatcagaaaa gtgctcatgg caagaaggga     540
cctattgatg tctctttcac gaactacgag ttctctcaat ctgctagctg aacgcctca     600 ctcgaaaccc ttgatttcac tgcacttcct gatatcttga acggtacttt ggccggttac     660
tctaccactc ccaacatttt ggaccctgag actgttcgac gtgttgattc ctatactggt     720
tacattgctc cttacactag ccgtaacaac ctcaatgttt tggccaacca taccgtctcc     780
cgcattcaat tgctcccaa gaatggtagc gaacctctca aggctaccgg tgttgaatgg     840
tatcccactg caacaagaa tcaaaagcaa attatcaagg cccgttatga agttatcatc     900
tcatctggtg ccattggtag tcctaagctt ttggaaatct ctggtatcgg taataaggat     960
atcgtctctg ctgctggtgt cgagtccttg attgacttgc ctggcgttgg ttccaacatg    1020
caagatcacg ttcatgctat cactgtctct actaccaata ttactggcta tactaccaac    1080
agcgtctttg tcaatgaaac ccttgcccaa gaacaaagag aagaatatga agccaacaag    1140
actggtatct gggctacttg tcccaacaac ctcggttatc ctacgcccga caactcttc    1200 aatggcaccg aattcgtttc tggaaaggag tttgctgaca agattcgtaa ctctactgat    1260
gaatgggcca actattatgc ttccaccaac gcctccaatg tcgagttatt aaagaagcaa    1320
tatgctattg tcgcctctcg ttacgaagag aactacttgt ctcctattga aatcaacttc    1380
actcctggtt atgagggtag cggtaatgtc gatttgcaaa acaacaagta ccaaactgtc    1440
aaccatgtct tgattgctcc tttaagtcgt ggttatactc acattaactc ttctgatgtg    1500
gaggatcatt ctgtcattaa tccccaatac tactctcatc ctatggatat tgatgtccat    1560
```

```
atcgcttcca ctaaacttgc tcgcgaaatc atcactgcct ctcccggtct tggtgacatt   1620
aacagtggcg aaatcgaacc cggtatgaat attacttctg acgacgacgt tagaaaatgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                               1926
```

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
tatcagaaaa gttgtcatgg caagaaggga                                     30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
agagacatca ataggtccct tcttgccatg                                     30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
cctgatatct tgtgcggtac tttggccggt                                     30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gggagtggta gagtaaccgg ccaaagtacc                                     30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cctggttatg aggacagcgg taatgtcgat                                     30

<210> SEQ ID NO 10
<211> LENGTH: 30
<212> TYPE: DNA

<213> ORGANISM: Artificial Sequence
<220> FEATURE:
<223> OTHER INFORMATION: primer

<400> SEQUENCE: 10
cttgttgttt tgcaaatcga cattaccgct                                    30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
cctggttatg aggaaagcgg taatgtcgat                                    30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
cctggttatg agcgtagcgg taatgtcgat                                    30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cctggttatg agaaaagcgg taatgtcgat                                    30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cctggttatg agaacagcgg taatgtcgat                                    30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cctggttatg agcagagcgg taatgtcgat                                    30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
cctggttatg agaccagcgg taatgtcgat                                    30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
cctggttatg agtgcagcgg taatgtcgat                                    30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
cctggttatg aggcgagcgg taatgtcgat                                    30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cctggttatg agtatagcgg taatgtcgat                                    30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
cctggttatg agtttagcgg taatgtcgat                                    30

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
cctggttatg agatgagcgg taatgtcgat                                    30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
cctggttatg aggtgagcgg taatgtcgat                                    30

<210> SEQ ID NO 23
<211> LENGTH: 30
<212> TYPE: DNA
<213> ORGANISM: Artificial Sequence
<220> FEATURE:

```
<223> OTHER INFORMATION: primer

<400> SEQUENCE: 23
cctggttatg agctgagcgg taatgtcgat                                          30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
cctggttatg agtggagcgg taatgtcgat                                          30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
cctggttatg agagcagcgg taatgtcgat                                          30

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
cctggttatg agcacagcgg taatgtcgat                                          30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
cctggttatg agattagcgg taatgtcgat                                          30

<210> SEQ ID NO 28
<211> LENGTH: 633
<212> TYPE: PRT
<213> ORGANISM: Mucor  guilliermondii

<400> SEQUENCE: 28

Met Lys Ile Ser Ala Ala Ile Val Thr Ile Ala Thr Ala Phe Ala Ser
 1               5                  10                  15

Leu Val Ser Ala Gln Ser Asn Thr Asp Thr Tyr Asp Tyr Val Ile Val
                20                  25                  30

Gly Gly Gly Val Gly Gly Leu Ala Leu Ala Asn Arg Leu Ser Glu Asn
            35                  40                  45

Lys Gln Val Thr Val Ala Val Leu Glu Ala Gly Pro Asn Ala Asn Asp
        50                  55                  60

Glu Phe Ile Val Tyr Ala Pro Gly Met Tyr Gly Gln Ala Val Gly Thr
 65                  70                  75                  80

Tyr Leu Ala Pro Leu Arg Pro Thr Val Pro Gln Glu Asn Met Asn Asn
                85                  90                  95
```

```
Arg Ser Leu Ser Ile Ala Thr Gly Lys Leu Leu Gly Gly Ser Ala
                100                 105                 110

Val Asn Gly Leu Val Trp Thr Arg Gly Ala Thr Lys Asp Phe Asp Ala
            115                 120                 125

Trp Glu Glu Leu Gly Asn Pro Gly Trp Asn Gly Ala Ser Met Phe Lys
    130                 135                 140

Tyr Phe Lys Lys Val Glu Asn Phe Thr Ala Pro Thr Pro Tyr Gln Val
145                 150                 155                 160

Asn Tyr Gly Ala Thr Tyr Gln Lys Asn Thr His Gly Tyr Lys Gly Pro
                165                 170                 175

Val Gln Val Ser Phe Thr Asn Tyr Glu Phe Pro Gln Ser Ala His Trp
            180                 185                 190

Asn Gln Ser Leu Ala Ser Leu Gly Phe Asp His Leu Pro Asp Leu Leu
    195                 200                 205

Asn Gly Thr Leu Ser Gly Tyr Ser Thr Thr Pro Asn Ile Leu Asp Pro
    210                 215                 220

Asn Thr Asp Gln Arg Cys Asp Ala Tyr Ala Ala Tyr Ile Ala Pro Tyr
225                 230                 235                 240

Thr Ala Arg Thr Asn Leu His Val Leu Ala Asn His Thr Val Ser Arg
                245                 250                 255

Ile Glu Phe Asn Gln Thr Asn Ala Asn Gln Pro Leu Val Ala Ser Gly
            260                 265                 270

Val Glu Trp Tyr Pro Thr Gly Asp Asn Thr Lys Lys Gln Thr Ile Lys
    275                 280                 285

Ala Arg Leu Glu Val Ile Val Ser Ser Gly Ser Ile Gly Ser Pro Lys
                290                 295                 300

Leu Leu Glu Ile Ser Gly Ile Gly Asn Lys Asp Ile Val Thr Ala Ala
305                 310                 315                 320

Gly Val Lys Ser Leu Leu Asp Leu Pro Gly Val Gly Ser Asn Met Gln
                325                 330                 335

Asp His Val His Ala Val Thr Val Ser Thr Thr Asn Ile Thr Gly Tyr
            340                 345                 350

Thr Thr Asp Ser Val Phe Val Asn Ser Thr Leu Ala Ser Glu Gln Arg
    355                 360                 365

Glu Gln Tyr Glu Lys Asp Lys Ser Gly Ile Trp Thr Thr Thr Pro Asn
    370                 375                 380

Asn Leu Gly Tyr Pro Thr Pro Ala Gln Leu Phe Asn Gly Thr Glu Phe
385                 390                 395                 400

Met Asp Gly Lys Ala Phe Ala Ala Arg Ile Arg Asn Ser Ser Gln Glu
                405                 410                 415

Trp Ala Gln Tyr Tyr Ala Ser Lys Asn Ala Ser Thr Val Glu Leu Leu
            420                 425                 430

Met Lys Gln Tyr Glu Ile Val Ala Ser Arg Tyr Glu Glu Asn Tyr Leu
    435                 440                 445

Ser Pro Ile Glu Ile Asn Leu Thr Pro Gly Tyr Gly Gly Val Gly Thr
    450                 455                 460

Val Asp Lys Thr Lys Asn Lys Tyr Gln Thr Val Asn His Val Leu Ile
465                 470                 475                 480

Ala Pro Leu Ser Arg Gly Phe Thr His Ile Asn Ser Ser Asp Ile Glu
                485                 490                 495

Asp Pro Val Asn Ile Asn Pro Gln Tyr Tyr Ser His Pro Met Asp Ile
            500                 505                 510
```

```
Asp Val His Val Ala Ser Thr Lys Leu Ala Arg Arg Ile Ile Asn Ala
            515                 520                 525

Pro Gly Leu Gly Asp Leu Asn Ser Gly Glu Val Glu Pro Gly Met Asp
        530                 535                 540

Ile Thr Ser Asp Ser Asp Val Arg Ala Trp Leu Ala Asn Asn Val Arg
545                 550                 555                 560

Ser Asp Trp His Pro Val Gly Thr Cys Ala Met Leu Pro Lys Glu Leu
                565                 570                 575

Gly Gly Val Val Asp Ser Ser Leu Lys Val Tyr Gly Thr Ala Asn Leu
                580                 585                 590

Arg Val Val Asp Ala Ser Ile Met Pro Leu Glu Val Ser Ser His Leu
            595                 600                 605

Met Gln Pro Thr Phe Gly Val Ala Glu Lys Ala Ala Asp Ile Ile Lys
        610                 615                 620

Ala Glu Tyr Lys Lys Gln Lys Ala Gln
625                 630

<210> SEQ ID NO 29
<211> LENGTH: 1902
<212> TYPE: DNA
<213> ORGANISM: Mucor  guilliermondii

<400> SEQUENCE: 29
atgaagattt ctgctgctat cgttaccatt gcaactgcat tcgcctcatt ggtttctgct      60
caaagtaaca ctgatactta cgattatgtt atcgtcggtg gtggtgttgg tggtttggct     120
ttagctaacc gtctttctga aacaagcag gttactgttg ctgttctcga agctggcccc     180
aacgctaatg acgaattcat tgtctatgct cctggcatgt atggtcaagc tgtcggtact     240
tacctcgctc ctctccgtcc taccgttcct caagaaaaca tgaacaacag atctctcagt     300
atcgctactg gtaaattatt aggtggtggt tctgctgtta acggtcttgt ctggactcgt     360
ggtgctacta aggatttcga tgcctgggag gaacttggta accctggttg aatggtgct     420 agtatgttca gtacttcaa gaaggtcgag aacttcactg ctcctactcc ttatcaagtc     480
aactatggtg ctacttatca aaagaacact cacggttata aggtcccgt tcaagtttct     540 ttcaccaact atgaattccc tcaatctgct cactggaacc aatctcttgc ttctcttggc     600
ttcgatcatc ttcccgatct cttgaacggt actcttagtg ttactctcac taccccttaac     660 attttggacc ctaatactga tcaacgttgt gatgcttatg ctgcttatat tgctccttac     720
actgctcgta ctaatcttca tgtcttggcc aaccacaccg tttctcgtat cgaattcaac     780
caaaccaacg ctaaccaacc tcttgttgcc tctggtgttg aatggtaccc tactggtgat     840
aacaccaaga agcaaactat taaggctcgt ttggaagtca ttgttttcctc cggttctatt     900 ggtagtccca gcttctcga atttccggt attggtaata aggacattgt cactgctgct     960
ggtgtcaagt ctttgctcga tttgcctggt gttggctcca acatgcaaga tcatgtccac    1020
gctgtcactg tttccaccac taacattacc ggttatacta ctgatagtgt ctttgtcaac    1080
tctactcttg cttctgaaca aagagaacaa tacgaaaagg ataagtctgg tatctggacc    1140
accaccccca taaccttggg ttatcctact cctgctcaac ttttcaacgg tactgaattc    1200
atggatggta aggcctttgc tgccagaatc cgtaactctt tcaagaatg gctcaatac    1260 tatgcttcca gaacgcttc tactgttgaa ttgttgatga agcaatacga aatcgttgcc    1320
agccgttacg aagaaaacta cttgtctcct attgaaatta acttgactcc cggttatggt    1380
ggtgttggta ccgttgataa gactaagaac aagtatcaaa ctgtcaacca cgtcttgatt    1440
```

```
gctcccttgt ctcgtggttt cactcatatt aactcttctg atatcgaaga ccccgttaac    1500
attaaccctc aatactactc tcaccctatg gatattgatg tccatgttgc ctctactaag    1560
cttgctcgtc gaatcattaa tgcccctggt cttggtgatc ttaacagtgg tgaagttgaa    1620
cccggtatgg atatcaccctc tgattctgat gtcagagctt ggttagctaa caacgttcgt    1680
tctgactggc atcccgtcgg tacttgtgct atgcttccca aggaacttgg tggtgttgtt    1740
gattcttctc ttaaggtcta cggtactgct aacttgagag ttgttgatgc ctccatcatg    1800
cctcttgaag tttcttctca cttgatgcaa cctacctttg gtgttgctga aaaggctgct    1860
gatattatca aggctgaata caagaagcaa aaggcccaat aa                        1902
```

<210> SEQ ID NO 30
<211> LENGTH: 635
<212> TYPE: PRT
<213> ORGANISM: Mucor hiemalis

<400> SEQUENCE: 30

```
Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
                20                  25                  30

Ile Val Gly Gly Gly Val Gly Gly Leu Ala Leu Ala Ser Arg Leu Ser
            35                  40                  45

Glu Asp Lys Ser Val Thr Val Ala Val Leu Glu Ala Gly Pro Asn Ala
        50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
                100                 105                 110

Ser Ala Ile Asn Gly Leu Val Trp Thr Arg Gly Ala Leu Lys Asp Phe
            115                 120                 125

Asp Ala Trp Glu Glu Leu Gly Asn Pro Gly Trp Asn Gly Arg Thr Met
        130                 135                 140

Phe Lys Tyr Phe Lys Lys Val Glu Arg Phe His Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
    210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285
```

```
Ile Lys Ala Arg Arg Glu Val Ile Val Ser Ser Ser Ile Gly Ser
    290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
                340                 345                 350

Gly Phe Thr Thr Asp Ser Val Phe Gln Asn Glu Thr Leu Ala Glu Glu
                355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
                420                 425                 430

Leu Leu Lys Lys Gln Tyr Ala Ile Val Ala Ser Arg Tyr Glu Glu Asn
                435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
                500                 505                 510

Asp Val Asp Val His Ile Ala Ser Thr Lys Leu Ala Arg Arg Ile Leu
                515                 520                 525

Gly Ala Glu Pro Gly Leu Ala Ser Ile Asn Ser Gly Glu Ile Gln Pro
530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
                580                 585                 590

Ala Asn Leu Arg Val Val Asp Ala Ser Ile Met Pro Leu Glu Ile Ser
                595                 600                 605

Ser His Leu Met Gln Pro Thr Tyr Gly Val Ala Glu Lys Ala Ala Asp
610                 615                 620

Ile Ile Lys Met Ser Arg Lys Asn Asn Asn
625                 630                 635

<210> SEQ ID NO 31
<211> LENGTH: 1908
<212> TYPE: DNA
<213> ORGANISM: Mucor hiemalis

<400> SEQUENCE: 31
atgaaaatct cagtagccat tgtcactatc gccgccgcct tcgcttcctt cgccaacgcc      60
caaaagaccg caaccagtaa tacctatgat tatgtaattg ttggtggtgg tgttggtggt     120
ttggcattag cctctagatt gtcagaagat aaatctgtca cagtagctgt tttagaagca     180
```

```
ggtcctaatg ccgacgaaca atttgttgtc tatgccccag gcatgtacgg tcaagctgtt      240
ggtaccgatt tgtgtccatt aagacctact gtcccacaag aagctatgaa taacagaaca      300
ttgaccatag caaccggtaa attgttaggt ggtggttcag ctatcaatgg tttggtttgg      360
actagaggtg cattaaagga ttttgacgcc tgggaagaat taggtaatcc aggttggaac      420
ggtagaacta tgttcaagta cttcaaaaag gttgaaagat ccatccacc tacaaaggct       480 caagtccaat atggtgcaac ctaccaaaaa ggtgtacacg gtaaaaatgg tagaatcgat      540
atttcttttc ctgaatttca attcccacaa tctgctaatt ggaacgcctc attggctacc      600
ttagatttca ctcatcaaca agacttgtta aatggttcct gcacggttta tagtactaca      660
cctaacacat tagatccaaa aaccgccaga agagttgact cctatacagg ttacattgct      720
cctttcgtta gtagaaagaa tttgttcgtc ttagcaaacc atactgtatc tagaatacaa      780
ttcaaaccaa gaatggtac agaattgttg aaggctgtcg gtgtagaatg gtacaccact       840
ggtgacaact caaacaaaca aacaattaag gcaagaagag aagttatcgt ctcttcaggt      900
tccattggta gtcctaaatt gttggaaata tccggtatcg gtaataagga tatcgtaact      960
gctgcaggtt tcaatctttt gattgatttg ccaggtgtag gttcaaacat gcaagaccat     1020
gttcacgctg taactgtttc cacaaccaac ataacaggtt ttactacaga tagtgttttc     1080
caaaacgaaa cattggcaga agaacaaaga caacaatact acaacaacaa accggtatc     1140 tggaccacta caccaaataa cttgggttat ccatccccta gtcaattatt tgatggtaca     1200
tctttcgaat caggtcaagc atttgcaaac agaattagaa actctaccga ccaatgggct     1260
gaatattacg catcaactaa tgccacaaac atcgaattgt tgaagaaaca atacgcaatc     1320
gttgcctcca gatacgaaga aaactacttg agtcctatcg aaatcaactt cactccaggt     1380
tatggtggta ccactgatgt tgatttgaaa aataacaagt accaaactgt taatcatgtc     1440
ttgatcgctc ctttatcaag aggttataca cacatcaatt ccagtaacat agaagatcct     1500
gtagttataa atccacaata ctacacccat ccaatggatg tcgacgtaca cattgcttct     1560
actaaattgg caagaagaat attaggtgcc gaacctggtt tggcttccat aaatagtggt     1620
gaaatccaac caggttctaa cattcatca gatgaagacg ttaagcaatg gttagcagat      1680
aatgttagat ctgactggca tcctgtcggt acatgcgcca tgttgccaag agaattaggt     1740
ggtgtcgtag atccaaattt gttggtttac ggtactgcaa acttaagagt tgtcgacgcc     1800
tctataatgc ctttggaaat ctcttcacat ttgatgcaac caacttacgg tgttgctgaa     1860
aaagccgctg atattattaa gatgtctaga aagaataaca taactaa                   1908
```

<210> SEQ ID NO 32
<211> LENGTH: 631
<212> TYPE: PRT
<213> ORGANISM: Mucor DR056860

<400> SEQUENCE: 32

Met Arg Leu Ser Val Ala Ile Leu Thr Leu Thr Ser Ala Leu Ala Ser
1               5                   10                  15

Val Thr Ser Ala Gln Gln Asn Asn Thr Asp Thr Tyr Asp Tyr Val Ile
            20                  25                  30

Val Gly Gly Gly Val Gly Gly Leu Ala Leu Ala Ser Arg Leu Ser Glu
        35                  40                  45

Asp Lys Asn Val Thr Val Ala Val Leu Glu Ser Gly Pro Tyr Ala Asp
    50                  55                  60

-continued

```
Asp Lys Phe Val Val Tyr Ala Pro Gly Met Tyr Gly Gln Ala Val Gly
 65                  70                  75                  80

Thr Asp Leu Cys Pro Leu Leu Pro Thr Val Pro Gln Pro Ser Met Asn
                 85                  90                  95

Asn Arg Thr Ile Thr Ile Ala Thr Gly Arg Leu Leu Gly Gly Gly Ser
            100                 105                 110

Ala Val Asn Gly Leu Val Trp Thr Arg Gly Ala Met Lys Asp Phe Asp
        115                 120                 125

Ala Trp Gln Glu Leu Gly Asn Pro Gly Trp Asn Gly Thr Thr Met Phe
    130                 135                 140

Lys Tyr Phe Lys Lys Ile Glu Asn Phe His Pro Pro Thr Glu Glu Gln
145                 150                 155                 160

Ile Gln Tyr Gly Ala Thr Tyr Asn Lys Ser Val His Gly Phe Asn Gly
                165                 170                 175

Pro Ile Asp Ile Ala Phe Pro Val Phe Glu Phe Pro Gln Ser Ala Asn
            180                 185                 190

Trp Asn Ala Ser Leu Ala His Leu Asn Phe Thr Arg Arg Gln Asp Leu
        195                 200                 205

Leu Asp Gly Ser Leu His Gly Tyr Ser Thr Thr Pro Asn Thr Leu Asn
    210                 215                 220

Pro Gln Thr Ala Arg Arg Ala Asp Ala Tyr Ala Gly Tyr Ile Gln Pro
225                 230                 235                 240

Asn Val Asn Arg Thr Asn Leu Ala Val Leu Ala Asn His Thr Val Ser
                245                 250                 255

Arg Ile Gln Phe Glu Ala Arg Asn Gly Ser Gln Pro Leu Lys Ala Ile
            260                 265                 270

Gly Val Glu Trp Tyr Thr Thr Gly Gly Asp Lys Thr Ser Lys Gln Thr
        275                 280                 285

Ile Lys Ala Arg Arg Glu Ile Ile Leu Ser Ser Gly Ala Ile Gly Ser
    290                 295                 300

Pro Lys Leu Leu Glu Val Ser Gly Ile Gly Asn Lys Ala Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Asp
            340                 345                 350

Gly Tyr Thr Thr Asn Ser Val Phe Thr Asn Glu Thr Leu Ala Gln Glu
        355                 360                 365

Gln Lys Asp Leu Tyr Tyr Asn Asn Lys Thr Gly Ile Trp Thr Thr Thr
    370                 375                 380

Pro Asn Asn Leu Gly Tyr Pro Ser Pro Ser Gln Leu Phe Thr Asn Thr
385                 390                 395                 400

Thr Phe Lys Ser Gly Lys Glu Phe Ala Ala Met Ile Arg Asn Ser Thr
                405                 410                 415

Asp Lys Tyr Ala Gln Tyr Ala Ala Asn Asn Ala Thr Asn Val Glu
            420                 425                 430

Leu Leu Lys Lys Gln Tyr Ser Ile Val Ala Arg Arg Tyr Glu Glu Asn
        435                 440                 445

Tyr Ile Ser Pro Ile Glu Ile Asn Phe Thr Pro Gly Tyr Gly Gly Thr
    450                 455                 460

Gly Met Ala Asp Leu Gln Asn Lys Lys Tyr Gln Thr Val Asn His Val
465                 470                 475                 480

Leu Val Ala Pro Leu Ser Arg Gly Tyr Thr His Ile Asn Ser Ser Asp
```

|  | 485 |  |  |  | 490 |  |  |  | 495 |  |  |
|---|---|---|---|---|---|---|---|---|---|---|---|
| Ile | Glu | Asp | Pro | Val | Ile | Asp | Pro | Gln | Tyr | Tyr | Ser | His | Pro | Leu |

Ile Glu Asp Pro Val Ile Asp Pro Gln Tyr Tyr Ser His Pro Leu
          500                    505                    510

Asp Val Asp Val His Val Ala Ser Thr Gln Leu Ala Arg Ser Ile Leu
       515                    520                    525

Asn Ala Pro Gly Leu Ala Ser Ile Asn Ser Gly Glu Val Glu Pro Gly
       530                    535                540

Glu Lys Val Gln Ser Asp Glu Asp Val Arg Lys Trp Leu Ser Asp Asn
545                    550                    555                560

Val Arg Ser Asp Trp His Pro Val Gly Thr Cys Ala Met Leu Pro Arg
             565                    570                575

Lys Leu Gly Gly Val Val Asp Ser Lys Leu Lys Val Tyr Gly Thr Ala
             580                    585                590

Asn Leu Arg Ile Val Asp Ala Ser Ile Ile Pro Leu Glu Ile Ser Ser
           595                    600                605

His Leu Met Gln Pro Val Tyr Ala Val Ser Glu Arg Ala Ala Asp Ile
   610                    615                    620

Ile Lys Ser Ser Ser Lys Lys
625                    630

<210> SEQ ID NO 33
<211> LENGTH: 1896
<212> TYPE: DNA
<213> ORGANISM: Mucor DR056860

<400> SEQUENCE: 33

```
atgcgtctct ctgtggcgat cctcactctc acttcggctc tggcttcggt tacctcggcc      60
caacaaaaca atactgatac ttatgactac gtgatcgtcg gaggaggagt gggtggactg     120
gctctcgctt cgcgcctctc cgaggataag aacgttaccg tggctgtcct ggaatcgggc     180
ccttatgcgg atgacaaatt cgtggtctac gccccaggga tgtatggtca ggctgtcgga     240
actgacctgt gtcctctgct cccaacggtt cctcaaccat ctatgaacaa tcgaaccatc     300
actattgcta cgggacgtct gctcggagga ggttcagctg tgaacggact ggtctggacc     360
cgtggagcta tgaaggattt cgacgcttgg caggagctgg aaacccagg atggaatggg     420
accactatgt tcaagtactt caagaaaatc gaaaacttcc atccccgac gaggaacag       480
attcaatacg cgctactta taacaagtct gtccacggtt caatggccc gatcgatatt       540
gcctttcccg tgttcgagtt ccgcagtct gctaactgga atgcgtcact ggcccatctc      600
aacttcacccc gccggcaaga tctgctcgac ggtagtctcc acggctacag cacgacccct    660
aacaccctga atccacagac tgcccgacgt gcggatgcct acgctggata tatccaacct    720
aacgtcaatc gaacgaacct ggctgtcctc gcgaatcata ccgttagtcg catccagttt    780
gaggcgcgga acgtagccaa ccactgaag gccattggcg tggaatggta tactacgggc     840
ggagacaaga ctagtaaaca gacgatcaag gcgcgccggg agatcattct gagtagcgga    900
gccattgggt cgcctaagct gctcgaagtg tccggatcg taacaaagc cattgttacc       960
gccgctggag tgcagtctct gatcgatctc ccaggcgttg gatcaaacat gcaagaccat    1020
gtgcacgctg ttaccgtgtc gaccactaat atcgatgggt acgaccaa ctccgtgttc      1080
acgaatgaga ccctcgccca ggaacaaaag gacctgtact acaacaacaa gactggaatc    1140
tggactacga cccctaacaa tctcgggtat cccagtccga gccagctgtt caccaacact    1200
acgtttaagt ctggcaaaga gtttgcggcc atgatccgca acagtactga taagtacgcc    1260
```

| | |
|---|---|
| cagtactatg ctgcgaacaa tgctacgaac gtcgagctgc tcaagaaaca atatagtatc | 1320 |
| gtggcccgac gttacgagga aaactacatc agccctatcg aaatcaactt cacgccagga | 1380 |
| tacgggggta ccgggatggc tgatctgcag aacaagaaat atcaaaccgt gaatcatgtc | 1440 |
| ctggttgccc ccctcagtcg gggctacact cacatcaact cgtccgatat tgaggacccc | 1500 |
| gttgtgatcg acccgcagta ctatagccat ccgctggatg tggacgtcca cgttgcgagt | 1560 |
| acccaactgg cccgaagcat cctcaacgcc cccggactgg cttctattaa ttcaggcgag | 1620 |
| gtggaaccgg gcgagaaggt ccagagcgat gaagacgttc gcaaatggct gtcggataac | 1680 |
| gtgcgttccg actggcatcc agtcggaacc tgcgctatgc tgccacgaaa gctcggagga | 1740 |
| gtcgttgatt cgaagctcaa agtctacggc accgcgaatc tgcgtatcgt tgacgcctcc | 1800 |
| atcattccgc tcgagatttc ttcacacctg atgcaaccag tctatgcggt ctccgaacgg | 1860 |
| gctgccgaca tcatcaaatc ctcctctaaa aataa | 1896 |

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
aactacgagt tccctcaatc tgctagctgg 30

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
gaactcgtag ttcgtgaaag agacatcaa 29

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
tgcacttcct gatctcttga acggtacttt 30

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
atcaggaagt gcagtgaaat caagggttt 29

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38

```
tgcacttcct gatatgttga acggtacttt                                    30
```

<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39

```
cggtactttg cacggttact ctaccactc                                     29
```

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40

```
tccaaaatgt tgggagtggt agagtaacc                                     29
```

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41

```
accactccca acaccttgga ccctgagact                                    30
```

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42

```
atcaacacgt tgaacagtct cagggtccaa                                    30
```

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43

```
accactccca acaacttgga ccctgagact                                    30
```

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44

```
accactccca acagcttgga ccctgagact                                    30
```

<210> SEQ ID NO 45
<211> LENGTH: 30
<212> TYPE: DNA

-continued

<213> ORGANISM: Artificial Sequence
<220> FEATURE:
<223> OTHER INFORMATION: primer

<400> SEQUENCE: 45
accactccca acgcattgga ccctgagact                                              30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
accactccca actgcttgga ccctgagact                                              30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
accactccca acgtcttgga ccctgagact                                              30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
tgcacttcct gatctcttgt gcggtacttt                                              30

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
atcaggaagt gcagtgaaat caagggttt                                               29

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
tgcacttcct gatatgttgt gcggtacttt                                              30

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
atcaacacgt cgaacagtct cagggtccaa                                              30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
tatcaaaaga actgccacgg ttataaaggt           30

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
agaaacttga acgggacctt tataaccgtg           30

<210> SEQ ID NO 54
<211> LENGTH: 30
<212> TYPE: DNA
<213> ORGANISM: Artificial Sequence
<220> FEATURE:
<223> OTHER INFORMATION: primer

<400> SEQUENCE: 54
cccgatctct tgtgcggtac tcttagtggt           30

<210> SEQ ID NO 55
<211> LENGTH: 29
<212> TYPE: DNA
<213> ORGANISM: Artificial Sequence
<220> FEATURE:
<223> OTHER INFORMATION: primer

<400> SEQUENCE: 55
aggggtagta gagtaaccac taagagtac            29

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
tctactaccc ctaacacctt ggaccctaat           30

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57 tagggtagt agagtaaccg ctaagagt              28

<210> SEQ ID NO 58
<211> LENGTH: 28
<212> TYPE: DNA
<213> ORGANISM: Artificial Sequence
<220> FEATURE:

<223> OTHER INFORMATION: primer

<400> SEQUENCE: 58
accaaaaagg ttgtcacggt aaaaatgg                                    28

<210> SEQ ID NO 59
<211> LENGTH: 29
<212> TYPE: DNA
<213> ORGANISM: Artificial Sequence
<220> FEATURE:
<223> OTHER INFORMATION: primer

<400> SEQUENCE: 59 ccttttttggt aggttgcacc gtattggac                                  29

<210> SEQ ID NO 60
<211> LENGTH: 29
<212> TYPE: DNA
<213> ORGANISM: Artificial Sequence
<220> FEATURE:
<223> OTHER INFORMATION: primer

<400> SEQUENCE: 60
aagacttgtt atgtggttcc ttgcacggt                                   29

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
taacaagtct tgttgatgag tgaaatctaa                                  30

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
tataacaagt cctgccacgg tttcaatggc                                  30

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
ggctatgtct atcgggccat tgaaaccgtg                                  30

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64
caagatctgc tctgcggtag tctccacggc                                  30

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
aggggtcgtg ctgtagccgt ggagactacc                                    30

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
cccggttatg gtgatgttgg tactgttgat                                    30

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
accaccataa ccgggagtca agttaatttc                                    30

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
cccggttatg gtcgtgttgg tactgttgat                                    30

<210> SEQ ID NO 69
<211> LENGTH: 30
<212> TYPE: DNA
<213> ORGANISM: Artificial Sequence
<220> FEATURE:
<223> OTHER INFORMATION: primer

<400> SEQUENCE: 69
cccggttatg gtaaagttgg tactgttgat                                    30

<210> SEQ ID NO 70
<211> LENGTH: 30
<212> TYPE: DNA
<213> ORGANISM: Artificial Sequence
<220> FEATURE:
<223> OTHER INFORMATION: primer

<400> SEQUENCE: 70
cccggttatg gtcatgttgg tactgttgat                                    30

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
cccggttatg gttctgttgg tactgttgat                                            30

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
ccaggttatg gtgataccac tgatgttgat                                            30

<210> SEQ ID NO 73
<211> LENGTH: 30
<212> TYPE: DNA
<213> ORGANISM: Artificial Sequence
<220> FEATURE:
<223> OTHER INFORMATION: primre

<400> SEQUENCE: 73
accataacct ggagtgaagt tgatttcgat                                            30

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
ccaggttatg gtcgtaccac tgatgttgat                                            30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
ccaggttatg gtaaaaccac tgatgttgat                                            30

<210> SEQ ID NO 76
<211> LENGTH: 30
<212> TYPE: DNA
<213> ORGANISM: Artificial Sequence
<220> FEATURE:
<223> OTHER INFORMATION: primer

<400> SEQUENCE: 76
ccaggttatg gtcataccac tgatgttgat                                            30

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
ccaggttatg gttctaccac tgatgttgat                                            30

<210> SEQ ID NO 78
<211> LENGTH: 30

<212> TYPE: DNA
<213> ORGANISM: Artificial Sequence
<220> FEATURE:
<223> OTHER INFORMATION: primer

<400> SEQUENCE: 78
ccaggatacg gggataccgg gatggctgat                              30

<210> SEQ ID NO 79
<211> LENGTH: 29
<212> TYPE: DNA
<213> ORGANISM: Artificial Sequence
<220> FEATURE:
<223> OTHER INFORMATION: primer

<400> SEQUENCE: 79
cccgtatcct ggcgtgaagt tgatttcga                               29

<210> SEQ ID NO 80
<211> LENGTH: 30
<212> TYPE: DNA
<213> ORGANISM: Artificial Sequence
<220> FEATURE:
<223> OTHER INFORMATION: primer

<400> SEQUENCE: 80
ccaggatacg ggcgtaccgg gatggctgat                              30

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
ccaggatacg ggaaaaccgg gatggctgat                              30

<210> SEQ ID NO 82
<211> LENGTH: 30
<212> TYPE: DNA
<213> ORGANISM: Artificial Sequence
<220> FEATURE:
<223> OTHER INFORMATION: primer

<400> SEQUENCE: 82
ccaggatacg ggcataccgg gatggctgat                              30

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
ccaggatacg ggagtaccgg gatggctgat                              30

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84

-continued accactccca acagtttgga ccctgagact                                30

<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85
accactccca acgccttgga ccctgagact                                30

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
accactccca actgtttgga ccctgagact                                30

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
gttgggagtg gtagagtaac cggccaaagt                                30

<210> SEQ ID NO 88
<211> LENGTH: 30
<212> TYPE: DNA
<213> ORGANISM: Artificial Sequence
<220> FEATURE:
<223> OTHER INFORMATION: primet

<400> SEQUENCE: 88
ccaggatacg ggtgtaccgg gatggctgat                                30

<210> SEQ ID NO 89
<211> LENGTH: 30
<212> TYPE: DNA
<213> ORGANISM: Artificial Sequence
<220> FEATURE:
<223> OTHER INFORMATION: primer

<400> SEQUENCE: 89
cccgtatcct ggcgtgaagt tgatttcgat                                30

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
ccaggatacg ggaataccgg gatggctgat                                30

<210> SEQ ID NO 91
<211> LENGTH: 30
<212> TYPE: DNA
<213> ORGANISM: Artificial Sequence
<220> FEATURE:
<223> OTHER INFORMATION: primer

<400> SEQUENCE: 91
actaccccta acagcttgga ccctaatact                                    30

<210> SEQ ID NO 92
<211> LENGTH: 30
<212> TYPE: DNA
<213> ORGANISM: Artificial Sequence
<220> FEATURE:
<223> OTHER INFORMATION: primer

<400> SEQUENCE: 92
aacggtactc ttcatggtta ctctactacc                                    30

<210> SEQ ID NO 93
<211> LENGTH: 30
<212> TYPE: DNA
<213> ORGANISM: Artificial Sequence
<220> FEATURE:
<223> OTHER INFORMATION: primer

<400> SEQUENCE: 93
aagagtaccg ttcaagaggt cgggaagatg                                    30

<210> SEQ ID NO 94
<211> LENGTH: 633
<212> TYPE: PRT
<213> ORGANISM: Mucor subtilissimus

<400> SEQUENCE: 94

Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
            20                  25                  30

Val Ile Val Gly Gly Gly Val Gly Gly Leu Ser Leu Ala Ser Arg Leu
        35                  40                  45

Ser Glu Asp Lys Gly Val Thr Val Ala Val Leu Glu Ser Gly Pro Tyr
50                  55                  60

Ala Asp Asp Arg Phe Val Val Tyr Ala Pro Gly Met Tyr Gly Gln Ala
65                  70                  75                  80

Val Gly Thr Glu Leu Cys Pro Leu Leu Pro Thr Val Pro Gln Val Gly
                85                  90                  95

Met Asn Asn Arg Thr Ile Thr Ile Ala Thr Gly Arg Leu Leu Gly Gly
            100                 105                 110

Gly Ser Ala Val Asn Gly Leu Val Trp Thr Arg Gly Ala Met Lys Asp
        115                 120                 125

Phe Asp Ala Trp Glu Glu Leu Gly Asn Pro Gly Trp Asn Gly Lys Thr
130                 135                 140

Met Phe Lys Tyr Phe Lys Lys Ile Glu Asn Phe His Pro Pro Thr Glu
145                 150                 155                 160

Glu Gln Val Gln Tyr Gly Ala Thr Tyr Gln Lys Asn Val His Gly Ser
                165                 170                 175

Gly Gly Pro Ile Asp Ile Ser Phe Pro Val Phe Glu Pro Gln Ser
            180                 185                 190

Ala Asn Trp Asn Ala Ser Leu Ala Tyr Leu Asn Phe Thr His Gln Gln
        195                 200                 205

Asp Leu Leu Asn Gly Ser Leu His Gly Tyr Ser Thr Thr Pro Asn Thr

```
            210                 215                 220
Leu Asn Pro Glu Thr Ala Arg Arg Ala Asp Ala Tyr Ala Gly Tyr Ile
225                 230                 235                 240

Gln Pro Asn Val Asn Arg Thr Asn Leu Ala Val Leu Ala Asn His Thr
                245                 250                 255

Val Ser Arg Ile Gln Phe Glu Lys Ser Asn Gly Ser Gln Pro Leu Lys
                260                 265                 270

Ala Ile Gly Val Glu Trp Tyr Thr Thr Gly Asp Lys Ser Thr Lys
                275                 280                 285

Gln Thr Ile Lys Ala Arg Arg Glu Val Ile Ile Ser Ser Gly Ala Ile
290                 295                 300

Gly Ser Pro Lys Leu Leu Glu Val Ser Gly Ile Gly Asn Lys Gln Ile
305                 310                 315                 320

Val Thr Ala Ala Gly Val Glu Ser Leu Ile Asp Leu Pro Gly Val Gly
                325                 330                 335

Ser Asn Met Gln Asp His Val His Ala Val Thr Val Ser Thr Thr Asn
                340                 345                 350

Ile Glu Gly Tyr Thr Thr Asn Ser Val Phe Thr Asn Glu Thr Leu Ala
                355                 360                 365

Gln Glu Gln Lys Asp Leu Tyr Tyr Asn Asn Lys Thr Gly Ile Trp Thr
                370                 375                 380

Thr Thr Pro Asn Asn Leu Gly Tyr Pro Ser Pro Ser Gln Leu Phe Thr
385                 390                 395                 400

Asn Thr Thr Phe Arg Ser Gly Lys Gln Phe Ala Ala Met Ile Arg Asn
                    405                 410                 415

Ser Thr Asp Lys Tyr Ala Gln Tyr Tyr Ala Ser Thr Lys Asn Ala Thr
                420                 425                 430

Asn Ile Gln Leu Leu Lys Lys Gln Tyr Ala Ile Val Ala Arg Arg Tyr
                435                 440                 445

Glu Glu Asp Tyr Ile Ser Pro Ile Glu Ile Asn Phe Thr Pro Gly Tyr
                450                 455                 460

Gly Gly Thr Gly Glu Val Asp Leu Gln Asn Asn Lys Tyr Gln Thr Val
465                 470                 475                 480

Asn His Val Leu Val Ala Pro Leu Ser Arg Gly Tyr Thr His Ile Asn
                    485                 490                 495

Ser Ser Asp Ile Glu Asp Pro Val Val Ile Asp Pro Gln Tyr Tyr Ser
                500                 505                 510

His Pro Leu Asp Val Asp Val His Val Ala Ser Thr Gln Leu Ala Arg
                515                 520                 525

Ser Ile Leu Asn Ala Pro Ala Leu Ala Ala Ile Asn Ser Gly Glu Val
                530                 535                 540

Glu Pro Gly Glu Lys Ile Gln Thr Asp Gln Asp Val Arg Lys Trp Leu
545                 550                 555                 560

Ser Asp Asn Val Arg Ser Asp Trp His Pro Val Gly Thr Cys Ala Met
                    565                 570                 575

Leu Pro Lys Gly Leu Gly Val Val Asp Ser Asn Leu Lys Val Tyr
                580                 585                 590

Gly Thr Ala Asn Leu Arg Val Val Asp Ala Ser Ile Ile Pro Leu Glu
                595                 600                 605

Ile Ser Ser His Leu Met Gln Pro Val Tyr Ala Val Ser Glu Arg Ala
                610                 615                 620

Ala Asp Ile Ile Lys Gly Ser Arg Asn
625                 630
```

<210> SEQ ID NO 95
<211> LENGTH: 637
<212> TYPE: PRT
<213> ORGANISM: Circinella simplex

<400> SEQUENCE: 95

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
        115                 120                 125

Asp Phe Asp Ala Trp Glu Glu Leu Gly Asn Pro Gly Trp Asn Gly Ala
    130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
        195                 200                 205

Pro Asp Leu Leu Asn Gly Thr Leu His Gly Tyr Ser Thr Thr Pro Asn
    210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
            260                 265                 270

Arg Ala Thr Gly Val Glu Trp Tyr Pro Thr Gly Asp Lys Ser Gln Lys
        275                 280                 285

Gln Val Leu Asn Ala Arg Tyr Glu Val Ile Leu Ser Ser Gly Ala Ile
    290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
            340                 345                 350

Ile Thr Gly Tyr Thr Thr Asn Ser Ile Phe Thr Asn Asp Ala Leu Ala
        355                 360                 365

Ala Glu Glu Arg Gln Glu Tyr Asp Asn Asn Lys Thr Gly Ile Tyr Thr

```
                370                 375                 380
Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
                420                 425                 430

Ala Glu Leu Leu Lys Lys Gln Tyr Ala Ile Ile Ala Ser Arg Tyr Glu
                435                 440                 445

Glu Asp Tyr Leu Ser Pro Ile Glu Ile Asn Leu Thr Pro Gly Tyr Gly
                450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
                500                 505                 510

Pro Met Asp Val Asp Val His Val Ala Ser Thr Lys Leu Ala Arg Glu
                515                 520                 525

Ile Ile Ser Ala Ser Pro Gly Leu Gly Asp Ile Asn Ser Gly Glu Thr
                530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
                580                 585                 590

Gly Thr Ser Asn Leu Arg Val Val Asp Ala Ser Val Met Pro Leu Glu
                595                 600                 605

Val Ser Ser His Leu Met Gln Pro Thr Phe Gly Ile Ala Glu Lys Ala
                610                 615                 620

Ala Asp Ile Ile Lys Ser Ala Asn Lys Lys Arg Ser Asn
625                 630                 635

<210> SEQ ID NO 96
<211> LENGTH: 637
<212> TYPE: PRT
<213> ORGANISM: Circinella sp.

<400> SEQUENCE: 96

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
                20                  25                  30

Tyr Val Ile Val Gly Gly Gly Val Gly Gly Leu Ala Leu Ala Ser Arg
                35                  40                  45

Leu Ser Glu Asn Lys Gly Val Ser Val Ala Val Leu Glu Ala Gly Pro
                50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
                100                 105                 110
```

-continued

Gly Gly Ser Ser Val Asn Gly Leu Val Trp Thr Arg Gly Leu Lys
         115                 120                 125

Asp Phe Asp Ala Trp Glu Glu Leu Gly Asn Pro Gly Trp Asn Gly Ala
130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
        195                 200                 205

Pro Asp Leu Leu Asn Gly Thr Leu His Gly Tyr Ser Thr Thr Pro Asn
210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
            260                 265                 270

Arg Ala Thr Gly Val Glu Trp Tyr Pro Thr Gly Asp Lys Ser Gln Lys
        275                 280                 285

Gln Val Leu Asn Ala Arg Tyr Glu Val Ile Leu Ser Ser Gly Ala Ile
    290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
            340                 345                 350

Ile Thr Gly Tyr Thr Thr Asn Ser Ile Phe Thr Asn Asp Ala Leu Ala
        355                 360                 365

Ala Glu Glu Arg Gln Glu Tyr Asp Asn Asn Lys Thr Gly Ile Tyr Thr
    370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
        435                 440                 445

Glu Asp Tyr Leu Ser Pro Ile Glu Ile Asn Leu Thr Pro Gly Tyr Gly
    450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510

Pro Met Asp Val Asp Val His Val Ala Ser Thr Lys Leu Ala Arg Glu
        515                 520                 525

Ile Ile Ser Ala Ser Pro Gly Leu Gly Asp Ile Asn Ser Gly Glu Thr

```
                  530                 535                 540
Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Asp Gly Val Val Asp Pro Asn Leu Lys Val Tyr
                580                 585                 590

Gly Thr Ser Asn Leu Arg Val Val Asp Ala Ser Val Met Pro Leu Glu
                595                 600                 605

Val Ser Ser His Leu Met Gln Pro Thr Phe Gly Ile Ala Glu Lys Ala
                610                 615                 620

Ala Asp Ile Ile Lys Ser Ala Asn Lys Lys Arg Ser Asn
625                 630                 635
```

<210> SEQ ID NO 97
<211> LENGTH: 644
<212> TYPE: PRT
<213> ORGANISM: Mucor circinelloides

<400> SEQUENCE: 97

```
Met Lys Ile Ser Ala Ala Ile Ile Thr Val Val Thr Ala Phe Ala Ser
1               5                   10                  15

Phe Ala Ser Ala Gln Gln Asp Thr Asn Asn Thr Ser Ser Thr Asp Thr
                20                  25                  30

Tyr Asp Tyr Val Ile Val Gly Gly Gly Val Ala Gly Leu Ala Leu Ala
                35                  40                  45

Ser Arg Ile Ser Glu Asn Lys Asp Val Thr Val Ala Val Leu Glu Ser
            50                  55                  60

Gly Pro Asn Ala Glu Asp Gln Phe Val Val Tyr Ala Pro Gly Met Tyr
65              70                  75                  80

Gly Gln Ala Val Gly Thr Glu Leu Ala Pro Leu Val Pro Thr Thr Pro
                85                  90                  95

Gln Glu Asn Met Gly Asn Arg Ser Leu Ser Ile Ala Thr Gly Arg Leu
                100                 105                 110

Leu Gly Gly Gly Ser Ala Val Asn Gly Leu Val Trp Thr Arg Gly Gly
                115                 120                 125

Leu Lys Asp Tyr Asp Ala Trp Glu Glu Leu Gly Asn Pro Gly Trp Asn
            130                 135                 140

Gly Ser Asn Leu Phe Lys Tyr Phe Lys Lys Val Glu Asn Phe His Pro
145                 150                 155                 160

Pro Thr Pro Ala Gln Ile Glu Tyr Gly Ala Thr Tyr Gln Lys Ser Ala
                165                 170                 175

His Gly Lys Asn Gly Pro Ile Asp Val Ser Phe Thr Asn Phe Glu Phe
                180                 185                 190

Pro Gln Ser Ala Lys Trp Asn Ala Ser Leu Glu Ser Leu Asp Phe Thr
                195                 200                 205

Ala Leu Pro Asp Leu Leu Asn Gly Thr Leu Ala Gly Tyr Ser Thr Thr
            210                 215                 220

Pro Asn Ile Leu Asp Pro Glu Thr Ala Arg Arg Val Asp Ala Tyr Ala
225                 230                 235                 240

Gly Tyr Ile Val Pro Tyr Met Gly Arg Asn Asn Leu Asn Val Leu Ala
                245                 250                 255

Asn His Thr Val Ser Arg Ile Gln Phe Ala Pro Gln Asn Gly Ser Glu
            260                 265                 270
```

```
Pro Leu Lys Ala Thr Gly Val Glu Trp Tyr Pro Thr Gly Asn Lys Asp
            275                 280                 285

Gln Lys Gln Thr Ile Lys Ala Arg Tyr Glu Val Ile Ile Ser Ser Gly
    290                 295                 300

Ala Ile Gly Ser Pro Lys Leu Leu Glu Ile Ser Gly Ile Gly Asn Lys
305                 310                 315                 320

Asp Ile Val Thr Ala Ala Gly Val Glu Ser Leu Ile Asp Leu Pro Gly
                325                 330                 335

Val Gly Ala Asn Met Gln Asp His Val His Ala Val Thr Val Ser Thr
            340                 345                 350

Thr Asn Ile Asp Gly Tyr Thr Thr Asn Ser Val Phe Thr Asn Glu Thr
            355                 360                 365

Leu Ala Gln Glu Gln Arg Glu Gln Tyr Glu Ala Asn Lys Thr Gly Ile
    370                 375                 380

Trp Thr Thr Thr Pro Asn Asn Leu Gly Tyr Pro Thr Pro Glu Gln Leu
385                 390                 395                 400

Phe Asn Gly Thr Glu Phe Val Ser Gly Lys Glu Phe Ala Ala Lys Ile
                405                 410                 415

Arg Asn Ser Thr Asp Glu Trp Ala Asn Tyr Tyr Ala Ser Thr Asn Ala
            420                 425                 430

Thr Asn Ala Asp Leu Leu Lys Lys Gln Tyr Ala Ile Val Ala Ser Arg
            435                 440                 445

Tyr Glu Glu Asn Tyr Leu Ser Pro Ile Glu Ile Asn Leu Thr Pro Gly
    450                 455                 460

Tyr Gly Gly Thr Gly Ser Pro Asp Leu Gln Asn Asn Lys Tyr Gln Thr
465                 470                 475                 480

Val Asn His Val Leu Ile Ala Pro Leu Ser Arg Gly Tyr Ala His Ile
                485                 490                 495

Asn Ser Ser Asp Ile Glu Glu Pro Ser Val Ile Asn Pro Gln Tyr Tyr
            500                 505                 510

Ser His Pro Leu Asp Ile Asp Val His Val Ala Ser Thr Lys Leu Ala
            515                 520                 525

Arg Glu Ile Ile Thr Ala Ser Pro Gly Leu Gly Asp Leu Asn Ser Gly
    530                 535                 540

Glu Val Glu Pro Gly Met Asn Val Thr Ser Glu Asp Asp Leu Arg Ser
545                 550                 555                 560

Trp Leu Ser Asn Asn Val Arg Ser Asp Trp His Pro Val Gly Thr Cys
                565                 570                 575

Ala Met Leu Pro Gln Glu Leu Gly Gly Val Val Ser Pro Ala Leu Met
            580                 585                 590

Val Tyr Gly Thr Ser Asn Leu Arg Val Val Asp Ala Ser Ile Met Pro
    595                 600                 605

Leu Glu Val Ser Ser His Leu Met Gln Pro Thr Tyr Gly Ile Ala Glu
    610                 615                 620

Lys Ala Ala Asp Ile Ile Lys Asn Tyr Tyr Lys Ser Gln Tyr Ser Gly
625                 630                 635                 640

Ala Gly Lys Asn
```